US008455540B2

(12) United States Patent
Mortier et al.

(10) Patent No.: US 8,455,540 B2
(45) Date of Patent: Jun. 4, 2013

(54) GOSSYPOL AND APOGOSSYPOL DERIVATIVES, PREPARATION THEREOF AND USES THEREOF

(75) Inventors: Jacques Mortier, Ecommoy (FR); Anne-Sophie Castanet, Le Mans (FR); Nguyet Trang Thanh Chau, Le Mans (FR)

(73) Assignee: Universite du Maine (Le Mans), Le Mans (FR)

( * ) Notice: Subject to any disclaimer, the term of this patent is extended or adjusted under 35 U.S.C. 154(b) by 29 days.

(21) Appl. No.: 12/746,339

(22) PCT Filed: Dec. 5, 2008

(86) PCT No.: PCT/FR2008/052216
§ 371 (c)(1),
(2), (4) Date: Aug. 23, 2010

(87) PCT Pub. No.: WO2009/080949
PCT Pub. Date: Jul. 2, 2009

(65) Prior Publication Data
US 2010/0331398 A1    Dec. 30, 2010

(30) Foreign Application Priority Data
Dec. 6, 2007   (FR) ..................... 07 08518

(51) Int. Cl.
*A61K 31/35* (2006.01)
*C07C 39/12* (2006.01)

(52) U.S. Cl.
USPC ............ 514/453; 514/700; 568/719; 568/441

(58) Field of Classification Search
USPC ........................ 514/453, 700; 568/719, 441
See application file for complete search history.

(56) References Cited

U.S. PATENT DOCUMENTS

| 7,799,782 | B2* | 9/2010 | Munson et al. ............ 514/234.5 |
| 7,812,058 | B2 | 10/2010 | Reed et al. |
| 2004/0214902 | A1* | 10/2004 | Wang et al. ..................... 514/700 |
| 2005/0209283 | A1 | 9/2005 | Hormann et al. |
| 2011/0111057 | A1 | 5/2011 | Reed et al. |
| 2012/0269901 | A1 | 10/2012 | Reed et al. |

FOREIGN PATENT DOCUMENTS

| EP | 1938816 A2 | 7/2008 |
| WO | 2005009434 A2 | 2/2005 |

OTHER PUBLICATIONS

Pellecchia's CAS: 155: 536307, 2011.*
Guo et al. CAS: 150: 398915, 2009.*
Chao-Yie et al. CAS: 144: 474911, 2006.*
Dodou et al. CAS: 143: 205761, 2005.*
Dao et al. CAS: 141: 235652, 2004.*
Nguyen et al. CAS: 137: 353192, 2002.*
Dao et al. CAS: 134: 5053, 2000.*
Dushanbieva et al. CAS: 99: 32870, 1983.*
Auelbekov et al. CAS: 105: 172144, 1986.*
Wang et al. CAS: 141:388644, 2004.*
P.C. Meltzer, P.H. Blickford, G.J.,Lambert: "A Regioselective Route to Gossypol and 5,5'-Didesiisopropyl-5,5'-diethylgossypol", Journal of Organic Chemistry, 1985, pp. 3121-3124, vol. 50, XP002487553.
M.B. Abou-Donia, J.W. Dieckert, C.M. Lyman: "Mass Spectrometry of Some Gossypol Ethers", Journal of Agricultural and Food Chemistry, 1970, pp. 534-535, vol. 18, XP002487554.
R.D. Stipanovic, A.A. Bell, M.E. Mace, C.R. Howell: "Antimicrobial Terpenoids of Gossypium: 6 Methoxygossypol and 6,6'-Dimethoxygossypol", Phytochemistry, 1975, pp. 1077-1081, vol. 14, XP002487555.
O.Gonzalez Correa, H.M. Cappi, C. Staffa: "New Gossypol Derivatives", Journal of American Oil Chemists' Society, 1966, pp. 678-680, vol. 43, XP002487556.
A.I. Meyers, J.J. Willemsen: "An Asymmetric Synthesis of (+)-Apogossypol Hexamethyl Ether", Tetrahedron Letters, 1996, pp. 791-792, vol. 37, No. 6, XP002487557.
S.A. Auelbekov, A.B. Mirzaabdullaev, D. KH. Aslanova, S. Kurchakov, G. SH. Achilova: "Synthesis and Antiviral Activity of Gossypol Derivatives", Pharm. Chem. Jour., 1985, pp. 479-481, vol. 19, No. 7, XP002487558.
V. Dao, C. Gaspard, M. Mayer, G.H. Werner, S. N. Nguyen, R. J. Michelot: "Synthesis and Cytotoxicity of Gossypol related Compounds", European Journal of Medicinal Chemistry, 2000, pp. 805-813, vol. 35, XP002487559.
D.A. Shirley, W.C. Sheeman: "The Structure and Reactions of Gossypol. III. Aliphatic Anil Derivatives of Gossypol", Journal of Organic Chemistry, 1956, pp. 251-252, vol. 21, XP002487560.
A.P. Hoffer, A. Agarwal, P. Meltzer, R. Naqvi,S.A. Matlin: "Antifertility, Spermicidal and Ultrastuctural Effects of Gossypol and Derivatives Administered Orally and by Intratesticular Injections", Contraception, 1988, pp. 301-331, vol. 37, No. 3, XP002487561.
J.D. Edwards, J.L. Cashaw: "Studies in the Naphthalene Series, III. Synthesis of Apogossypol Hexamethyl Ether", Journal of the American Chemical Society, 1956, pp. 2283-2285, vol. 79, XP002487564.
P. Prince, K.L. Evans, V.M. Rosas-Garcia, R.D. Gandour, F.R. Fronczek: "Molecules for Intramolecular Recognition. 2. Synthesis and Structures of Dinaphthyl and Arylnaphthylenes",Tetrahedron Letters, 1992, pp. 6431-6434, vol. 33, XP002487918.
B.A Keay; D.K.W. Lee, R. Rodrigo: "A New Method for the Generation of Isobenzofurans: A Simple Entry to Substituted Naphthalenes", Tetrahedron Letters, 1980, pp. 3663-3666, vol. 21, XP002487919.
A.I. Meyers, J.J. Willemsen: "An Oxazoline Based Approach to (S)-Gossypol", Tetrahedron, 1998, pp. 10493-10511, vol. 54, XP002487920.
International Search Report in Corresponding Application No. PCT/FR2008/052216 Dated May 18, 2009.
Badawy et al., "Gossypol Inhibits Proliferation of Endometrioma Cells in Culture", Asian Journal of Andrology, 2007, vol. 9, No. 3, pp. 388-393.

(Continued)

Primary Examiner — Rei-tsang Shiao
(74) Attorney, Agent, or Firm — Young & Thompson

(57) ABSTRACT

Gossypol and apogossypol derivatives of general formula (1), preparation thereof and use thereof.

30 Claims, No Drawings

OTHER PUBLICATIONS

Balakrishnan et al., "Gossypol, a BH3 Mimetic, Induces Apoptosis in Chronic Lymphocytic Leukemia Cells", American Society of Hematology, Blood, 2008, vol. 112, No. 5, pp. 1971-1980.

Etxebarria et al., "Regulation of Antiapoptotic MCL-1 Function by Gossypol: Mechanistic Insights from in Vitro Reconstituted Systems", Biochemical Pharmacology, vol. 76, 2008, pp. 1563-1576.

Karaca et al., "Profiling of Angiogenic Cytokines Produced by Hormone and Drug-Refractory Prostate Cancer Cell Lines, PC-3 and DU-145 Before and After Treatment With Gossypol", Eur. Cytokine Netw., vol. 9, No. 4, Dec. 2008, pp. 176-184.

Kitada et al., "Bcl-2 Antagonist Apogossypol (NSC736630) Displays Single-Agent Activity in Bcl-2-Transgenic Mice and Has Superior Efficacy With Less Toxicity Compared With Gossypol (NSC19048)", American Society of Hematology, Blood, 2008, vol. 111, pp. 3211-3219.

Kline et al., "R-(−)-Gossypol (AT-101) Activates Programmed Cell Death in Multiple Myeloma Cells", Experimental Hematology, 2008, vol. 36, pp. 568-576.

Ko et al., "Gossypol Reduction of Tumor Growth Through ROS-Dependent Mitochondria Pathway in Human Colorectal Carcinoma Cells", Int. J. Cancer, 2007, vol. 121, pp. 1670-1679.

Li et al., "Synergistic Cytotoxicity of Bcl-xL Inhibitor Gossypol and Chemotherapeutic Agents in Non-Hodgkin's Lymphoma Cells", Cancer Biology & Therapy, Jan. 2008, vol. 7, No. 1, pp. 51-60.

Marzo et al., "Bcl-2 Family Members as Molecular Targets in Cancer Therapy", Biochemical Pharmacology, 2008, vol. 76, pp. 939-946.

Meng et al., "Natural BH3 Mimetic (−)-Gossypol Chemosensitizes Human Prostate Cancer Via Bcl-xL Inhibition Accompanied by Increase of Puma and Noxa", Molecular Cancer Therapeutics, 2008, vol. 7, pp. 2192-2202.

Macoska et al., "-(−)Gossypol Promotes the Apoptosis of Bladder Cancer Cells in Vitro", Pharmacological Research, 2008, vol. 58, pp. 323-331.

Moon et al., "Gossypol Suppresses Telomerase Activity in Human Leukemia Cells Via Regulating hTERT", FEBS Letters, 2008, vol. 582, pp. 3367-3373.

Stipanovic et al., "Effect of Racemic, (+) -and (−)-Gossypol on Survival and Development of *Heliothis virescens* Larvae", Physiological Ecology, Environ. Entomol., 2008, vol. 37, No. 5, pp. 1081-1085.

Ye et al., "Modulation of Multidrug Resistance Gene Expression in Human Breast Cancer Cells by (+)-Gossypol-enriched Cottonseed Oil", Anticancer Research, 2007, vol. 27, pp. 107-116.

Zhang et al., "Gossypol Induces Apoptosis in Human PC-3 Prostate Cancer Cells by Modulating Caspase-Dependent and Caspase-Independent Cell Death Pathways", Life Sciences, 2007, vol. 80, pp. 767-774.

Zhang et al., "Differential Growth Inhibition and Induction of Apoptosis by Gossypol Between Hct116 and Hct116/Bax-/-Colorectal Cancer Cells", Clinical and Experimental Pharmacology and Physiology, 2007, vol. 34, No. 3, pp. 230-237.

* cited by examiner

GOSSYPOL AND APOGOSSYPOL DERIVATIVES, PREPARATION THEREOF AND USES THEREOF

The present invention relates to the development of novel chemical compounds in particular having an application as anticancer agents. More particularly, the present invention relates to gossypol derivatives, methods of synthesis of these derivatives and uses thereof.

For many years the applicant has been developing novel methodological tools of organometallic chemistry and is interested in particular in metallation reactions, which permit regioselective functionalization of aromatic rings. Thus, operating conditions permitting metallation of benzoic acids without prior protection of the carboxylic acid function have been developed by the applicant (a) Gohier, F.; Mortier, J. *J. Org. Chem.* 2003, 68, 2030. (b) Gohier, F.; Castanet, A.-S.; Mortier, J. *J. Org. Chem.* 2005, 70, 1501. (c) Tilly, D.; Samanta, S. S.; De, A.; Castanet, A.-S.; Mortier, *J. Org. Lett.* 2005, 7, 827. (d) Tilly, D.; Castanet, A.-S.; Mortier, J. *Tetrahedron Lett.* 2006, 47, 1121. (e) Nguyen, T. H.; Chau, N. T. T.; Castanet, A.-S.; Nguyen, K. P. P.; Mortier, J. *J. Org. Chem.* 2007, 72, 3419. (f) Castanet, A.-S.; Tilly, D.; Véron, J.-B.; Samanta, S. S.; De, A.; Ganguly, T.; Mortier, J. *Tetrahedron* 2008, 64, 3331. (g) Chau, N. T. T.; Nguyen, T.-H.; Castanet, A.-S.; Nguyen, K. P. P.; Mortier, J. *Tetrahedron* 2008, 64, 10552). Experimental conditions making it possible to modify the metallation site and propose selective methods of synthesis of variously substituted aromatic compounds have been obtained. In this work, the synthesis of a natural product, gossypol, and some of its derivatives was investigated. Gossypol (1,1',6,6',7,7'-hexahydroxy-5,5'-diisopropyl-3,3'-dimethyl-2,2'-binaphthalene-8,8'-dicarboxaldehyde) is the main pigment in cottonseeds. Enormous quantities of cotton are produced each year, so there have always been attempts to utilize the natural gossypol thus obtained (about 50,000 tonnes/year). This oxygen-containing binaphthalene with $C_2$ symmetry exists in two atropoisomeric forms (R) and (S). Cleavage of the 2,2' bond gives two identical binaphthyl assemblies. Gossypol is shown below in Diagram 1:

Diagram 1

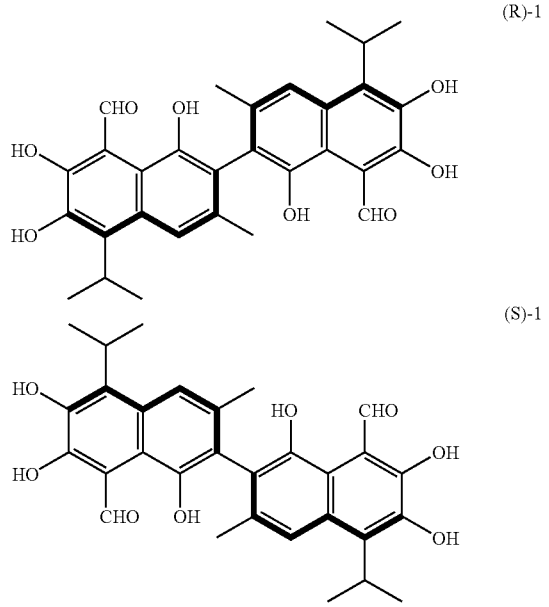

The extensive bibliographical data concerning the biological activities of gossypol and its derivatives show that its activity might be linked to the presence of the free phenolic groups at 6,6' and 7,7' on the binaphthalene system. Indeed, blocking of these phenol functions by methoxyether derivatives dispels all toxicity. The toxicity of gossypol is also thought to be associated with the aldehyde functions or with the presence of an electrophilic function of the enamine type in this same position.

In the literature, numerous prodrugs and deoxygenated gossypol derivatives have been synthesized. However, the applicant is only aware of a single complete asymmetric synthesis of (S)-gossypol (see reference 22). Derivatives of apogossypol are also described in WO2005/009434. The development of novel active molecules is a recurrent technical challenge, and one of the objectives of the present invention is to provide novel active ingredients, in particular pharmaceutical for the treatment of cancers or for the treatment of viral or dermatologic disorders, having the advantage of not being toxic at the doses used in the body, and only exerting their cytotoxic effect when in contact with cancer cells.

A subject of the present invention is to propose novel gossypol and apogossypol derivatives, which are interesting novel symmetric or asymmetric compounds. The compounds of the invention are gossypol derivatives in which, in particular, the isopropyl and methyl groups are replaced with functions that are structurally similar (ethyl, n-propyl, n-butyl, etc.) or more remote (esters, alkoxy, alkylsulphenyl, sulphonyl, etc.).

A further subject of the present invention is to propose several syntheses of the compounds of the invention. The invention in particular relates to an asymmetric synthesis, a complete asymmetric synthesis, a racemic synthesis and a complete racemic synthesis of the compounds of the invention.

The invention also relates to the preparation of certain intermediates, and if applicable said novel intermediates.

The invention also relates to the use of at least one compound of the invention or of at least one enantiomer of a compound of the invention, or of a salt of such a compound, enantiomeric or racemic, or a prodrug of such a compound, enantiomeric or racemic, as a medicament, or in a pharmaceutical composition in combination with any pharmaceutically acceptable excipient.

In particular, the invention relates to at least one compound of the invention or to at least one enantiomer of a compound of the invention, or to a salt of such a compound, enantiomeric or racemic, or a prodrug of such a compound, enantiomeric or racemic, for the manufacture of a medicament intended for the treatment of a cancer or of a parasitic disease or of a viral disease or of a dermatologic disease, in a person needing said treatment, or for the manufacture or of a contraceptive product, in particular intended for males.

The invention also relates to the use of at least one compound of the invention or of at least one enantiomer of a compound of the invention, or of a salt of such a compound, enantiomeric or racemic, or a prodrug of such a compound, enantiomeric or racemic, as anticancer, in particular antitumour, active ingredient, in particular for their activity as ligand of proteins of the Bcl-2 family, for treating a patient who has a cancer, in particular selected from a colon cancer or colorectal cancer, a melanoma, a lung cancer, a glioblastoma, an adenocarcinoma, a leukaemia, a prostate cancer or a breast cancer.

The invention also relates to the use of at least one compound of the invention or of at least one enantiomer of a compound of the invention, or of a salt of such a compound, enantiomeric or racemic, or a prodrug of such a compound, enantiomeric or racemic, as antiviral active ingredient for the treatment of viral infections due in particular to the herpes simplex type 2 virus, the influenza virus and the parainfluenza virus, and HIV-1.

The compounds are particularly indicated for the treatment of patients refractory to other treatments, in particular for antiviral treatments.

The invention also relates to the use of at least one compound of the invention or of at least one enantiomer of a compound of the invention, or of a salt of such a compound, enantiomeric or racemic, or a prodrug of such a compound, enantiomeric or racemic, as active ingredient for the treatment of dermatologic disorders, in particular psoriasis.

The invention also relates to a phytopharmaceutical composition comprising at least one compound of the invention or at least one enantiomer of a compound of the invention, or a salt of such a compound, enantiomeric or racemic, or a prodrug of such a compound, enantiomeric or racemic, in combination with any phytopharmaceutically acceptable excipient.

The invention further relates to the use of at least one compound of the invention or of at least one enantiomer of a compound of the invention, or of a salt of such a compound, enantiomeric or racemic, or a prodrug of such a compound, enantiomeric or racemic, as an antifungal agent, for making an antifungal product.

The compounds of the invention are also useful as pigments, in colouring or pigmenting compositions.

The compound of the invention corresponds to general formula (I)

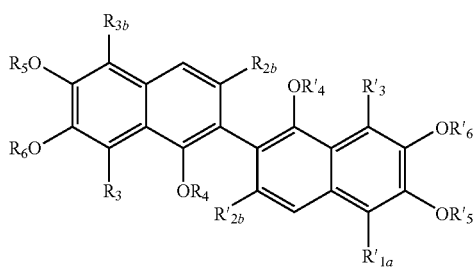

in which $R_{1b}$ and $R'_{1b}$ are each independently methyl, ethyl, n-propyl, isopropyl, n-butyl, t-butyl, s-butyl, isobutyl, pentyl or hexyl, $R_{2b}$ and $R'_{2b}$ are each independently a linear or branched alkyl with 1 to 6 carbon atoms, optionally substituted, or an ester, preferably, $R_{2b}$ and $R'_{2b}$ are each independently methyl, ethyl, n-propyl, isopropyl, n-butyl, s-butyl, isobutyl, t-butyl, pentyl, or hexyl, $R_3$ and $R'_3$ are each independently a hydrogen or CHO or any group capable of being transformed in vivo to release a hydrogen or a CHO, in particular $R_3$ and $R'_3$ can be independently a $CR_8{=}NR_9$ or $C(O)OR_{10}$ group in which $R_8$, $R_9$ and $R_{10}$ are independently a hydrogen atom or a linear or branched alkyl with 1 to 20 (for example 1 to 6) carbon atoms, optionally substituted, preferably methyl, ethyl, n-propyl, isopropyl, n-butyl, s-butyl, t-butyl, n-pentyl, n-hexyl, n-heptyl, n-$C_{12}H_{25}$, $CH_2{-}CH(CH_3){-}C_6H_5$, $CH{-}(COOCH_3){-}CH_2C_6H_5$, $CH{-}(CH_2OH){-}CH_2C_6H_5$ or a linear or branched alkenyl with 2 to 20 carbon atoms, optionally substituted; and $R_4$, $R'_4$, $R_5$, $R'_5$, $R_6$ and $R'_6$ are each independently a hydrogen or a protective group of the hydroxy function, gossypol, apogossypol and compounds in which simultaneously $R_{1b}$, $R'_{1b}$ are ethyl and $R_2$, $R'_2$ are methyl being excluded, or one of its enantiomers, or one of its salts, or a salt of one of its enantiomers or one of its prodrugs.

According to a first embodiment, the compounds of the invention correspond to general formula (1), in which $R_{1b}$ and $R'_{1b}$ are identical and optionally, $R_3$ and $R'_3$ are identical and/or $R_{2b}$ and $R'_{2b}$ are identical. Advantageously, the compounds of the invention are symmetric, which means that $R_{1b}$ and $R'_{1b}$ are identical, $R_3$ and $R'_3$ are identical and $R_{2b}$ and $R'_{2b}$ are identical.

According to another embodiment $R_{1b}$ and $R'_{1b}$ are identical, $R_3$ and $R'_3$ are different and $R_{2b}$ and $R'_{2b}$ are identical.

According to another embodiment $R_{1b}$ and $R'_{1b}$ are identical, $R_3$ and $R'_3$ are identical and $R_{2b}$ and $R'_{2b}$ are different.

According to another embodiment, the compounds of the invention correspond to general formula (1) in which $R_{1b}$ and $R'_{1b}$ are different and optionally, $R_3$ and $R'_3$ are identical and/or $R_{2b}$ and $R'_{2b}$ are identical.

According to another embodiment, the compounds of the invention correspond to general formula (1) in which $R_{1b}$ and $R'_{1b}$ are different, $R_3$ and $R'_3$ are identical and $R_{2b}$ and $R'_{2b}$ are identical.

According to another embodiment, the compounds of the invention correspond to general formula (1) in which $R_{1b}$ and $R'_{1b}$ are different, $R_3$ and $R'_3$ are different and $R_{2b}$ and $R'_{2b}$ are identical.

According to another embodiment, the compounds of the invention correspond to general formula (1) in which $R_{1b}$ and $R'_{1b}$ are different, $R_3$ and $R'_3$ are different and $R_{2b}$ and $R'_{2b}$ are different.

According to a third embodiment, the compounds of the invention correspond to general formula (1) in which $R_{1b}$ and $R'_{1b}$ are different and optionally, $R_3$ and $R'_3$ are identical and/or $R_{2b}$ and $R'_{2b}$ are different.

According to a preferred embodiment, neither $R_{1b}$ nor $R'_{1b}$ is isopropyl.

According to a preferred embodiment, $R_3$ and $R'_3$ are each a hydrogen, $R_{1b}$, $R'_{1b}$, $R_{2b}$, $R'_{2b}$ are each a methyl or an ethyl, n-propyl, isopropyl, n-butyl, s-butyl, t-butyl, n-pentyl, n-hexyl, $R_4$, $R'_4$, $R_5$, $R'_5$, $R_6$ and $R'_6$ are each independently a hydrogen.

According to a preferred embodiment $R_{1b}$ and $R'_{1b}$ are each independently methyl, n-propyl, isopropyl, n-butyl, s-butyl, t-butyl, isobutyl, $R_{2b}$ and $R'_{2b}$ are each methyl, and $R_3$ and $R'_3$ are each independently a hydrogen or CHO; preferably, $R_{1b}$ and $R'_{1b}$ are identical and/or $R_3$ and $R'_3$ are identical.

According to a preferred embodiment $R_{1b}$ and $R'_{1b}$ are each methyl, $R_{2b}$ and $R'_{2b}$ are each independently methyl, ethyl, n-propyl, isopropyl, n-butyl, s-butyl, t-butyl, isobutyl, and $R_3$ and $R'_3$ are each independently a hydrogen or CHO; preferably, $R_{2b}$ and $R'_{2b}$ are identical and/or $R_3$ and $R'_3$ are identical.

According to a preferred embodiment $R_{1b}$ and $R'_{1b}$ are each ethyl, $R_{2b}$ and $R'_{2b}$ are each independently ethyl, n-propyl, isopropyl, n-butyl, s-butyl, t-butyl, isobutyl, and $R_3$ and $R'_3$ are each independently a hydrogen or CHO; preferably, $R_{2b}$ and $R'_{2b}$ are identical and/or $R_3$ and $R'_3$ are identical.

According to a preferred embodiment $R_{1b}$ and $R'_{1b}$ are each n-propyl, $R_{2b}$ and $R'_{2b}$ are each independently methyl, ethyl, n-propyl, isopropyl, n-butyl, s-butyl, t-butyl, isobutyl, $R_3$ and $R'_3$ are each independently a hydrogen or CHO; preferably, $R_{2b}$ and $R'_{2b}$ are identical and/or $R_3$ and $R'_3$ are identical.

According to a preferred embodiment $R_{1b}$ and $R'_{1b}$ are each isopropyl, $R_{2b}$ and $R'_{2b}$ are each independently ethyl, n-propyl, isopropyl, n-butyl, s-butyl, t-butyl, isobutyl, and $R_3$ and $R'_3$ are each independently a hydrogen or CHO; preferably, $R_{2b}$ and $R'_{2b}$ are identical and/or $R_3$ and $R'_3$ are identical.
Compounds that are particularly preferred are those in Table 1 below.
TABLE 1
| Composé | Formule |
|---|---|
| I | 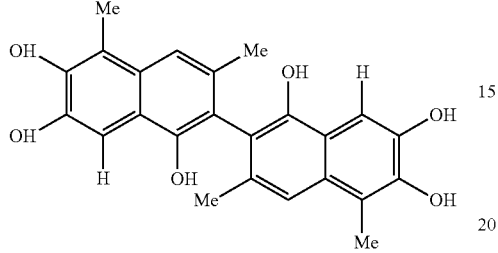 |
| II | 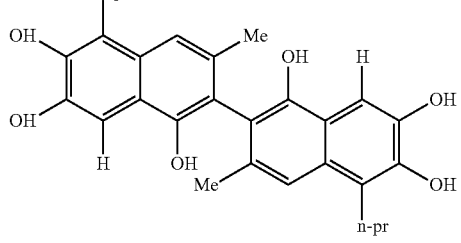 |
| III | 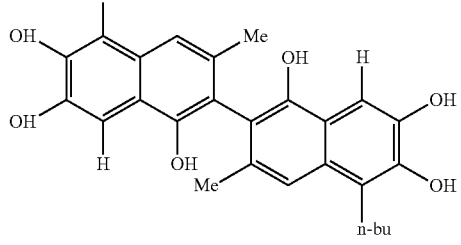 |
| IV | 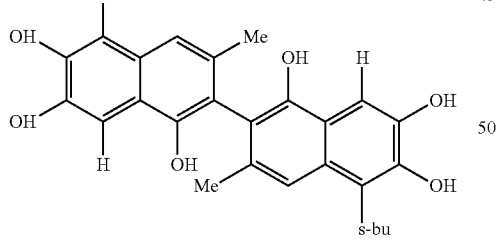 |
| V | 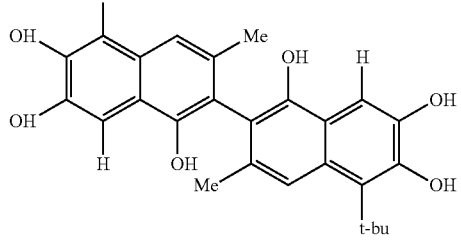 |
TABLE 1-continued
| Composé | Formule |
|---|---|
| VI | 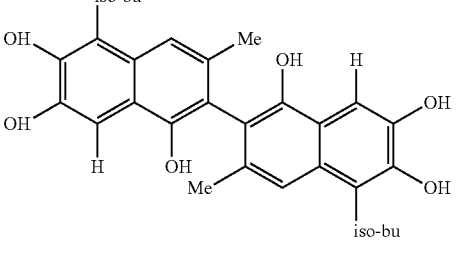 |
| VII | 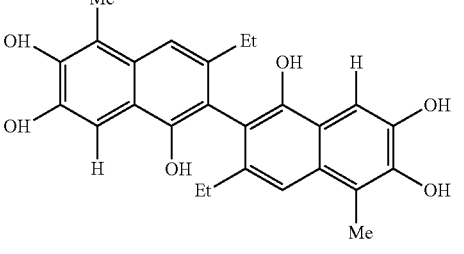 |
| VIII | 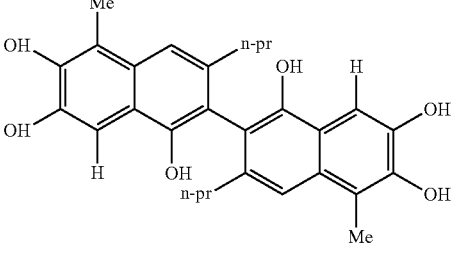 |
| IX | 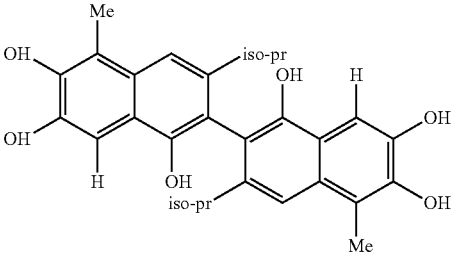 |
| X | 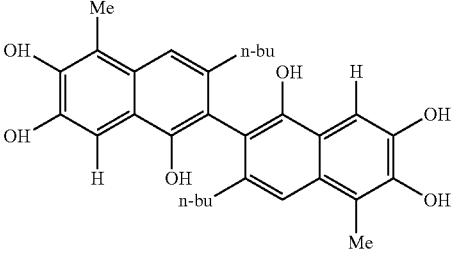 |
| XI | 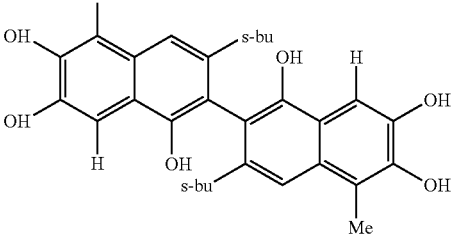 |

TABLE 1-continued
| Composé | Formule |
|---|---|
| XII | 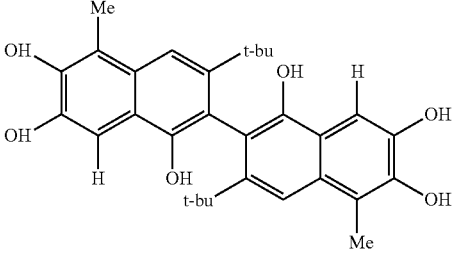 |
| XIII | 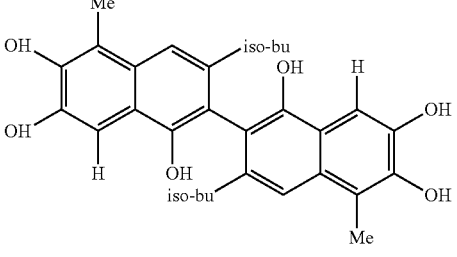 |
| XIV | 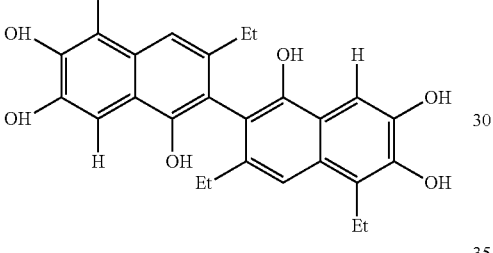 |
| XV | 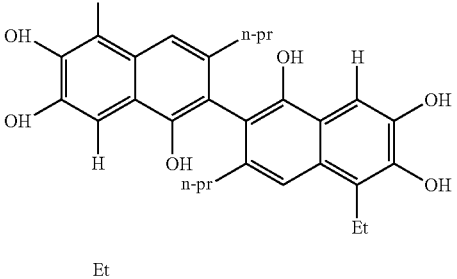 |
| XVI | 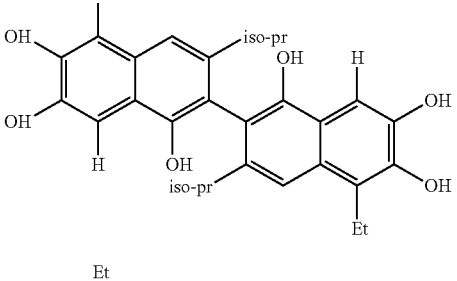 |
| XVII | 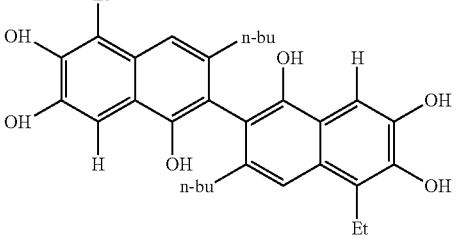 |
| XVIII | 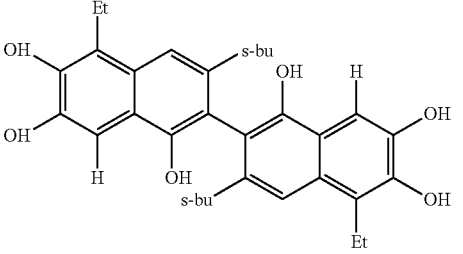 |
| XIX | 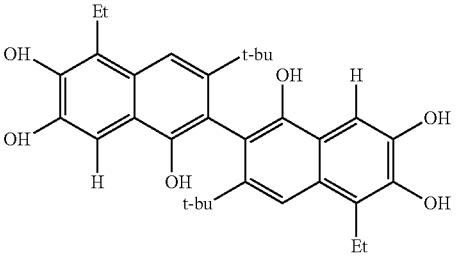 |
| XX | 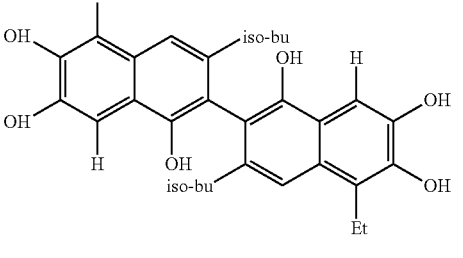 |
| XXI | 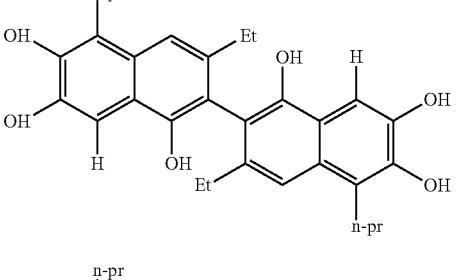 |
| XXII | 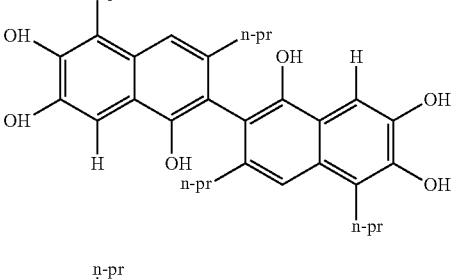 |
| XXIII | 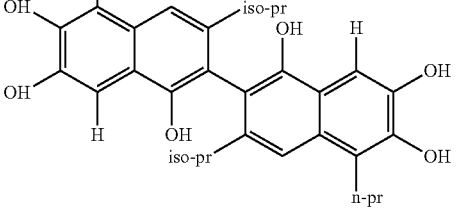 |

TABLE 1-continued
| Composé | Formule |
|---|---|
| XXIV | 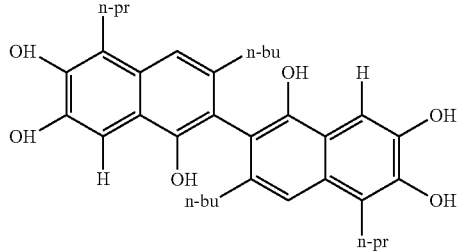 |
| XXV | 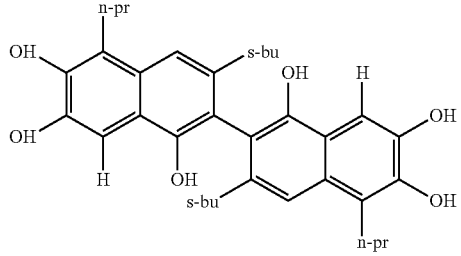 |
| XXVI | 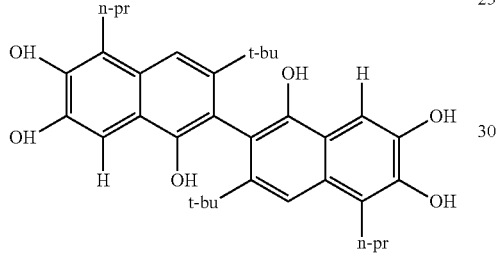 |
| XXVII | 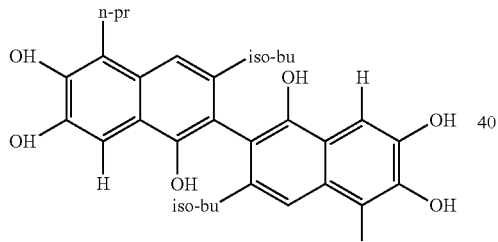 |
| XXVIII | 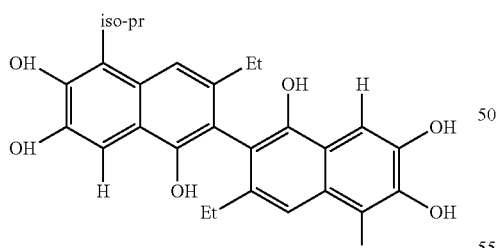 |
| XXIX | 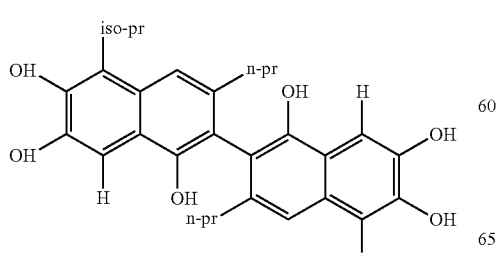 |
| XXX | 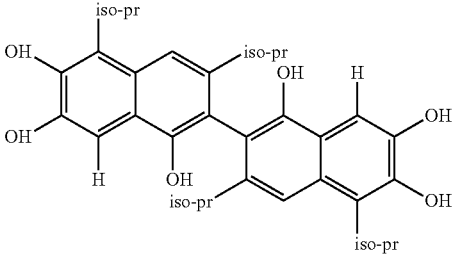 |
| XXXI | 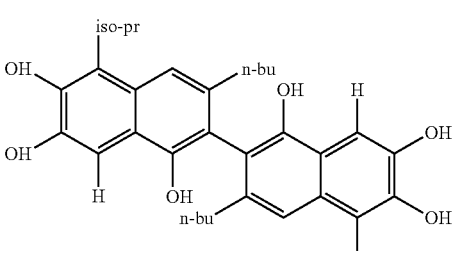 |
| XXXII | 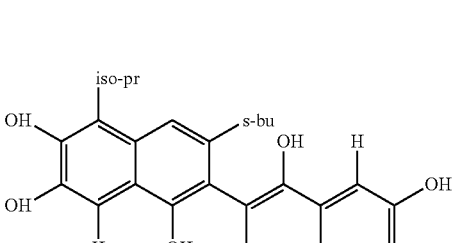 |
| XXXIII | 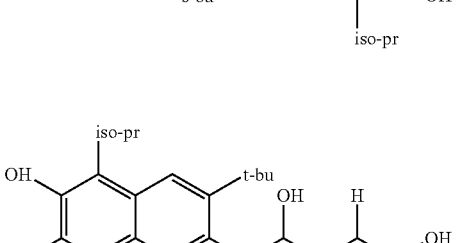 |
| XXXIV | 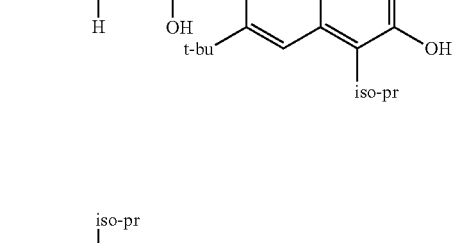 |

TABLE 1-continued
| Composé | Formule |
|---|---|
| XXXV | 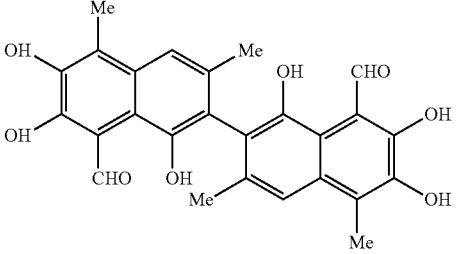 [SMILES: Cc1cc2c(C)c(O)c(O)c(C=O)c2c(O)c1-c1c(C)cc2c(C)c(O)c(O)c(C=O)c2c1O] |
| XXXVI | 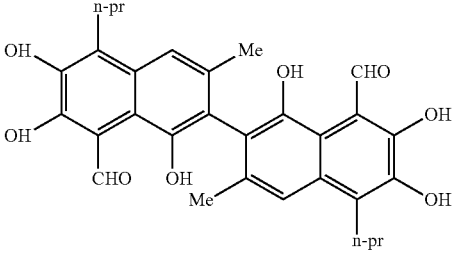 |
| XXXVII | 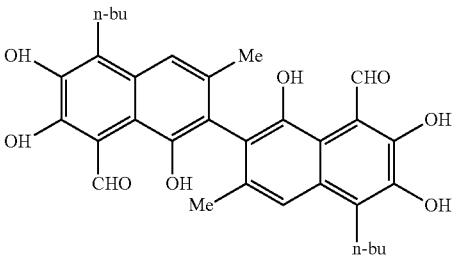 |
| XXXVIII | 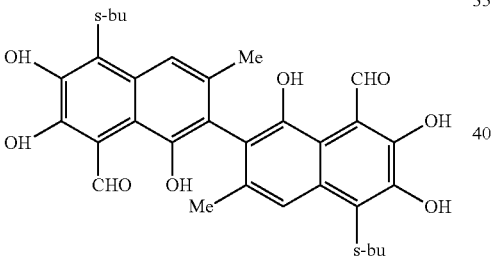 |
| XXXIX | 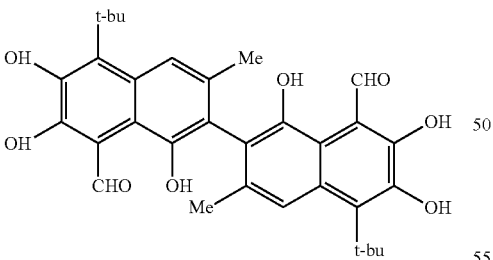 |
| XL | 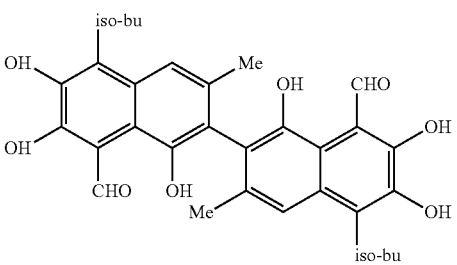 |
| XLI | 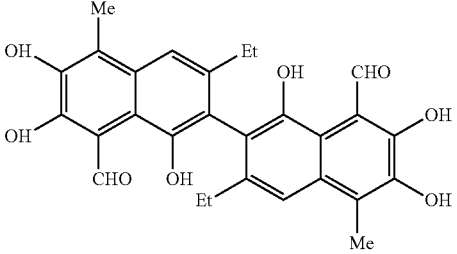 |
| XLII | 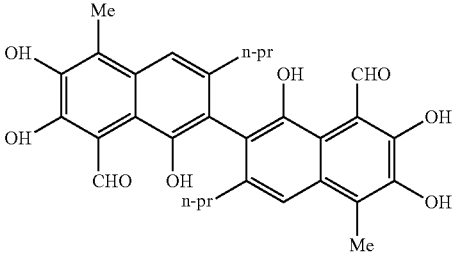 |
| XLIII | 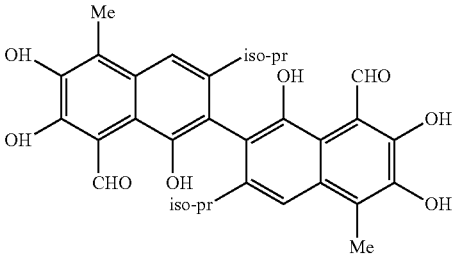 |
| XLIV | 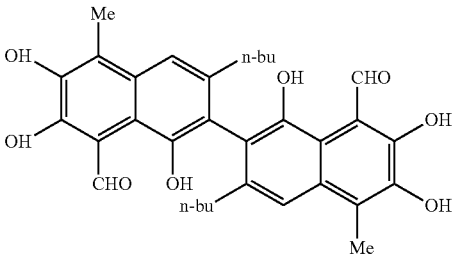 |
| XLV | 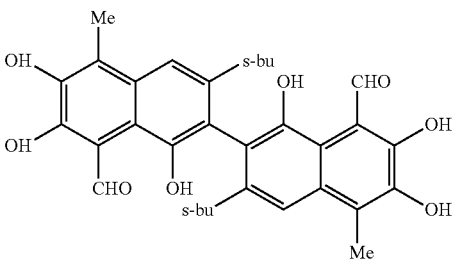 |
| XLVI | 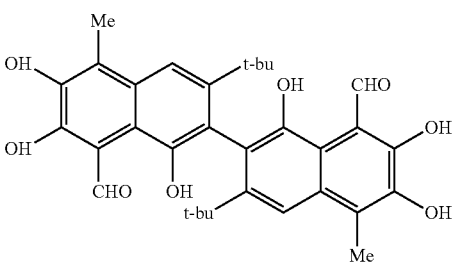 |

TABLE 1-continued
| Composé | Formule |
|---|---|
| XLVII | 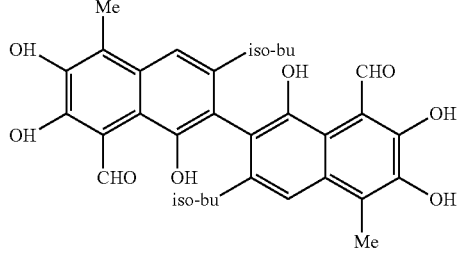 |
| XLVIII | 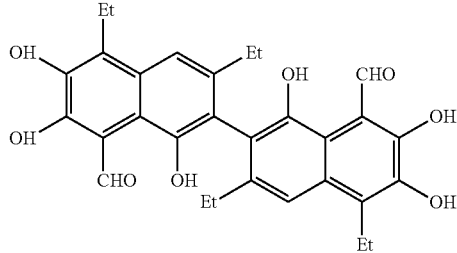 [SMILES: CCc1cc2c(CC)c(O)c(O)c(C=O)c2c(O)c1-c1c(CC)cc2c(CC)c(O)c(O)c(C=O)c2c1O] |
| XLIX | 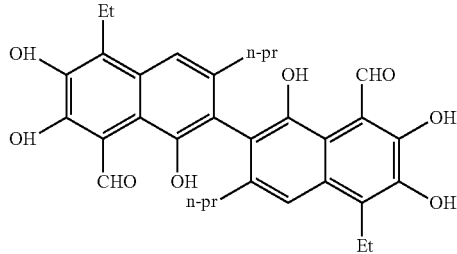 |
| L | 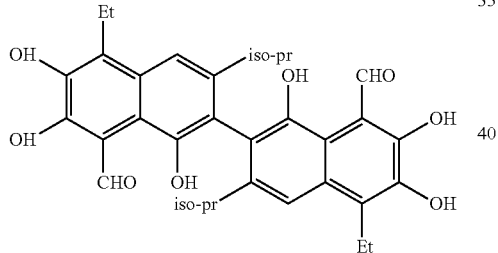 |
| LI | 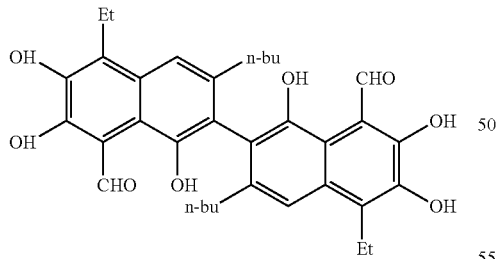 |
| LII | 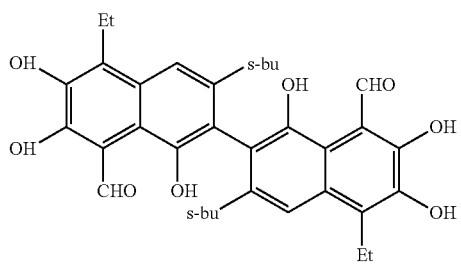 |
| LIII | 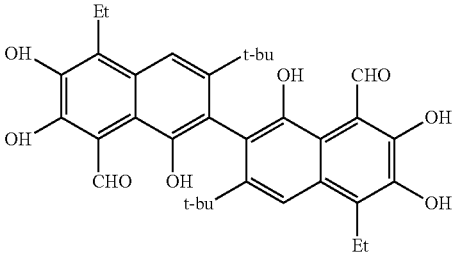 |
| LIV | 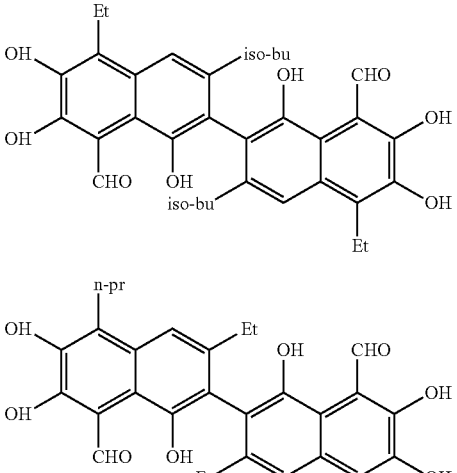 |
| LV | 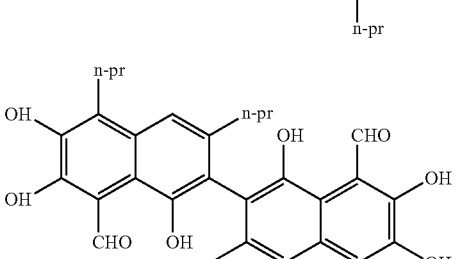 |
| LVI | 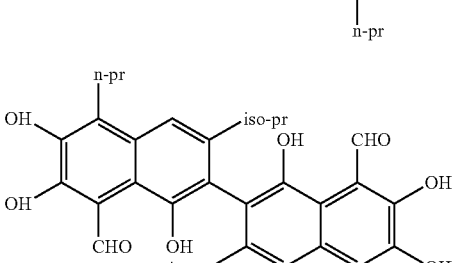 |
| LVII | 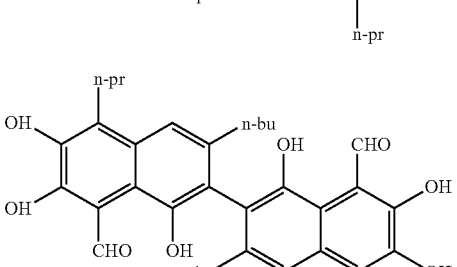 |
| LVIII | |

TABLE 1-continued

| Composé | Formule |
|---|---|
| LIX | 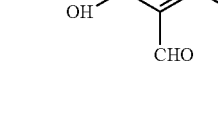 |
| LX | |
| LXI | |
| LXII | |
| LXIII | |
| LXIV | |

TABLE 1-continued

| Composé | Formule |
|---|---|
| LXV | 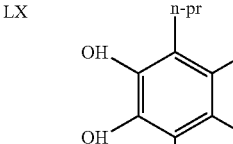 |
| LXVI | |
| LXVII | |
| LXVIII | |

In the present invention, the term "optionally substituted" means unsubstituted or substituted with 1 to 3 groups, which may be identical or different, selected from a linear or branched alkyl with 1 to 6 carbon atoms, preferably methyl, ethyl, n-propyl, isopropyl, n-butyl, t-butyl, s-butyl, isobutyl, linear or branched polyhaloalkyl with 1 to 6 carbon atoms, linear or branched alkoxy with 1 to 6 carbon atoms, hydroxy, carboxy, linear or branched alkoxycarbonyl with 1 to 6 carbon atoms, linear or branched acyloxy with 1 to 6 carbon atoms, formyl, linear or branched acyl with 1 to 6 carbon atoms, aroyl, amido, nitro, cyano, thiol, or halogen atoms.

In the present invention, the term "metallable group" means any group functionalizable by metallation, in particular any group possessing an acid H. By "metallation" is meant the direct replacement of a hydrogen atom with a metal atom in an organic molecule, to form a carbon-metal bond; metallation can also be carried out by a reaction of halogen (Br or I)-lithium exchange (see reference 25).

In the present invention, the term "protective group of the hydroxy function" means an alkyl, benzyl, acetyl, tosyl, trityl, silyl group or any equivalent group known by a person skilled in the art to be able to protect a hydroxy function.

In the present invention, the term "prodrug" means any compound that is a metabolic precursor of a compound of the invention, namely any compound that can be transformed in vivo to release an effective quantity of an active compound of the invention that is pharmaceutically acceptable, said transformation being a chemical transformation, enzymatic transformation or any other transformation leading to the release in vivo of the compound of the invention. A prodrug can be inactive when it is administered to the subject. The prodrugs of the compounds of the invention can be determined easily by a person skilled in the art, using known techniques of the prior art. The preferred prodrugs of the invention include the ester and imine derivatives of the compounds of the invention.

According to the present invention, preferred compounds are those corresponding to formula (1) in which $R_4$, $R'_4$, $R_5$, $R'_5$, $R_6$ and $R'_6$ are each a hydrogen or a protective group of the hydroxy function, $R_{1b}$, $R'_{1b}$, $R_{2b}$, $R'_{2b}$ are each independently a linear or branched alkyl with 1 to 6 carbon atoms, preferably methyl, ethyl, n-propyl, isopropyl, n-butyl, t-butyl, s-butyl, isobutyl, and $R_3$ and $R'_3$ are each independently a hydrogen or CHO; gossypol and apogossypol and the compounds in which simultaneously $R_{1b}$, $R'_{1b}$ are ethyl and $R_2$, $R'_2$ are methyl being excluded.

Other preferred compounds are those corresponding to formula (1) in which $R_4$, $R'_4$, $R_5$, $R'_5$, $R_6$ and $R'_6$ are each a hydrogen, and $R_{1b}$, $R'_{1b}$, $R_{2b}$, $R'_{2b}$ are each independently a linear alkyl, preferably a methyl, an ethyl or an n-propyl or an n-butyl, and $R_3$ and $R'_3$ are each independently a hydrogen or CHO; gossypol and apogossypol and the compounds in which simultaneously $R_{1b}$, $R'_{1b}$ are ethyl and $R_2$, $R'_2$ are methyl being excluded.

The invention also relates to a method for the preparation of the compounds of formula (1) in which $R_{1b}$ and $R'_{1b}$ are each independently a linear or branched alkyl with 1 to 6 carbon atoms, optionally substituted, a linear or branched alkoxy with 1 to 6 carbon atoms, optionally substituted, or an ester, preferably, $R_{1b}$ and $R'_{1b}$ are each independently methyl, ethyl, n-propyl, isopropyl, n-butyl, t-butyl, s-butyl, isobutyl, pentyl or hexyl; $R_{2b}$ and $R'_{2b}$ are each independently a linear or branched alkyl with 1 to 6 carbon atoms, optionally substituted, a linear or branched alkoxy with 1 to 6 carbon atoms, optionally substituted, or an ester, preferably, $R_{2b}$ and $R'_{2b}$ are each independently methyl, ethyl, n-propyl, isopropyl, n-butyl, s-butyl, isobutyl, t-butyl, pentyl or hexyl; $R_3$ and $R'_3$ are each independently a hydrogen or CHO or any group capable of being transformed in vivo to release a hydrogen or a CHO, in particular $R_3$ and $R'_3$ can be independently a $CR_8=NR_9$ or $C(O)OR_{10}$ group in which $R_8$, $R_9$ and $R_{10}$ are independently a hydrogen atom or a linear or branched alkyl with 1 to 20 carbon atoms, optionally substituted, or a linear or branched alkenyl with 2 to 20 carbon atoms, optionally substituted; and $R_4$, $R'_4$, $R_5$, $R'_5$, $R_6$ and $R'_6$ are each independently a hydrogen, a linear or branched alkyl with 1 to 20 carbon atoms, optionally substituted, or a protective group of the hydroxy function, gossypol and apogossypol being excluded. Preferred compounds of formula (1) are those described above. A general description of methods of preparation of the compounds of formula (1) is given below. In the following description of the method, unless specified otherwise, all the substituents are as defined for the compounds of formula (1).

A characteristic feature of the method of the invention is that it employs at least one metallation reaction.

According to a particular embodiment of the invention, the method is a complete synthesis starting from compound 8, of general formula

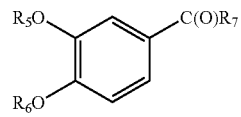

8 in which $R_5$ and $R_6$ are each independently a linear or branched alkyl with 1 to 6 carbon atoms optionally substituted or a protective group of the hydroxy function and $R_7$ is OH, or O (linear or branched alkyl with 1 to 6 carbon atoms). Preferably, $R_5$ and $R_6$ are each a methyl and compound 8 is veratric acid.

Advantageously, in a first step of the method of complete synthesis of the invention, the compound of formula 8 is subjected to a metallation reaction in position 2, without needing to protect the acid function, and the metallation reaction is followed by a substitution reaction, to give the product of general formula 7 below,

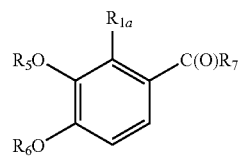

7 in which $R_5$ and $R_6$ are each independently a hydrogen, a linear or branched alkyl with 1 to 6 carbon atoms optionally substituted or a protective group of the hydroxy function, preferably, $R_5$ and $R_6$ are each a methyl; $R_7$ is OH, or O (linear or branched alkyl with 1 to 6 carbon atoms; and $R_{1a}$ is a metallable group, preferably $R_{1a}$ is methyl.

Starting from compound 7, naphthoic acid 4, in which $R_3$ is H, can be prepared by a Dieckmann condensation. This preparation is known by a person skilled in the art. Molecule 5 can be synthesized from any compound 4 by means that are known by a person skilled in the art. In order to show in the rest of the method that 4 and 5 can have different substituents, the substituents of 5 are identified differently from those of 4. Compounds 4 and 5 correspond to the following general formula,

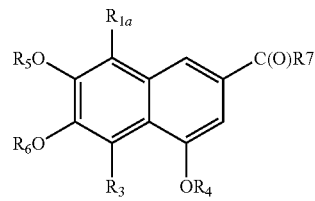

4

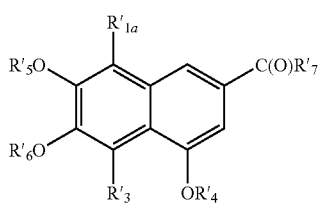

5 in which $R_{1a}$ is a metallable group, preferably an alkyl group functionalizable by metallation, preferably a methyl, $R_4$, $R'_4$, $R_5$, $R'_5$, $R_6$ and $R'_6$ are each independently a hydrogen, a linear or branched alkyl with 1 to 6 carbon atoms, optionally substituted, preferably methyl, ethyl, n-propyl, isopropyl, n-butyl, s-butyl, isobutyl, or a protective group of the hydroxy function, $R_3$ and $R'_3$ are each independently a hydrogen and $R_7$ is OH, or O (linear or branched alkyl with 1 to 6 carbon atoms).

Preferably, $R_5$ and $R_6$ are each a methyl, $R_7$ is OH, and compound 8 is veratric acid.

According to a particular embodiment of the invention, the $R_{1a}$ group of compound 4 can be subjected to a metallation reaction, to give compound 6 of general formula

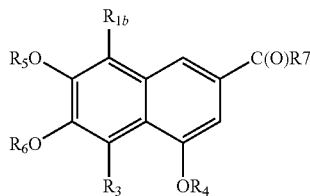

6 in which $R_{1b}$ is a linear or branched alkyl with 1 to 6 carbon atoms, optionally substituted, preferably ethyl, n-propyl, isopropyl, n-butyl, s-butyl, isobutyl; preferably, $R_{1b}$ is not a methyl; more preferably, $R_{1b}$ is a group which is not metallable, preferably an alkyl group that does not have acid hydrogen on alpha of the naphthalene ring, $R_4$, $R_5$, and $R_6$ are each independently a hydrogen, a linear or branched alkyl with 1 to 6 carbon atoms, optionally substituted, preferably methyl, ethyl, n-propyl, isopropyl, n-butyl, s-butyl, isobutyl, or a protective group of the hydroxy function, $R_3$ is a hydrogen and $R_7$ is OH, or O (linear or branched alkyl with 1 to 6 carbon atoms.

According to a particular embodiment of the invention, the two naphthalene subunits 4 and 5 can be condensed to give the lactone 3, the general formula of which is shown below and the substituents of which have the definitions stated above for compounds 4 and 5. According to a particular embodiment, this condensation is permitted by a metallation reaction, by which a metal atom, preferably a bromine atom, tin atom or silicon atom, is inserted in compound 4, between functions $C(O)R_7$ and $OR_4$. According to another embodiment of the invention, the condensation can also be carried out by a classical electrophilic substitution reaction (bromination).

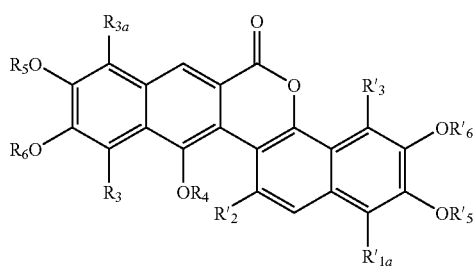

3

According to a preferred embodiment of the invention, the lactone 3 then undergoes an asymmetric reduction by any means known by a person skilled in the art, preferably an asymmetric reduction employing an asymmetric catalyst, in particular compound 11 below, or alternatively by the application of chiral oxazaborolidines.

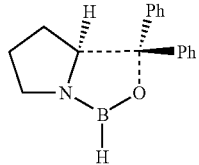

11

The asymmetric reduction of 3, optionally followed by substitution reactions, gives compound 2, which corresponds to the following general formula

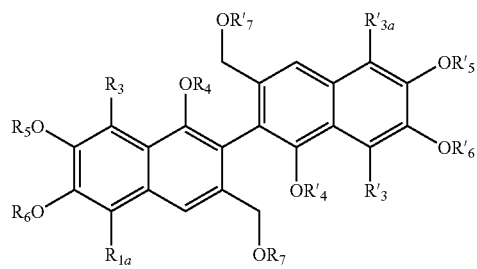

2 in which $R_{1a}$ and $R'_{1a}$ are each independently a metallable group, preferably an alkyl group functionalizable by metallation, preferably a methyl, $R_4$, $R'_4$, $R_5$, $R'_5$, $R_6$ and $R'_6$ are each independently a hydrogen, a linear or branched alkyl with 1 to 6 carbon atoms, optionally substituted, preferably methyl, ethyl, n-propyl, isopropyl, n-butyl, s-butyl, isobutyl, or a protective group of the hydroxy function, $R_3$ and $R'_3$ are each independently a hydrogen, $R_7$ and $R'_7$ are each independently a hydrogen or a linear or branched alkyl with 1 to 6 carbon atoms, optionally substituted, preferably methyl, ethyl, n-propyl, isopropyl, n-butyl, s-butyl, isobutyl, or a protective group of the hydroxy function.

According to a first embodiment, the compounds of general formula 2 can optionally be metallated at $R_{1a}$ to give the compounds of formula 1. However, in the case when $R_{1b}$ is $R_{1a}$, the compounds of formula 2 can be regarded as compounds of formula 1.

According to another embodiment, compound 2 can be reduced at the functions $CH_2OR_7$, then optionally metallated to give the corresponding compound where $CH_2OR_7$ is transformed to $R_{2b}$ and $R'_{2b}$.

According to another preferred embodiment of the invention, two functions $R_3$ and $R'_3$ different from H, can be introduced simultaneously after construction of the binaphthalene 2 in which $R_3$ and $R'_3$ are each independently a hydrogen atom, to give a compound of formula 1 in which $R_3$ is a CHO group. The preferred reaction conditions are DMF, POCl3 (cf. reference 21).

The three embodiments given above can be carried out successively, or alternately, depending on the desired compound. According to a preferred embodiment, the transformation of $R_3$ is the last step.

Complete Asymmetric Synthesis

Thus, the invention relates to a complete asymmetric synthesis of the compounds of general formula 1; in this synthesis the starting product is the compound of general formula 8 in which $R_5$ and $R_6$ are each independently a protective group of the hydroxy function; and preferably veratric acid or a salt thereof; said method of complete synthesis comprising at least one step of metallation of compound 8 in position 2 of the ring, said step of metallation in position 2 of ring 8 preferably involving the reagent LTMP (lithium 2,2,6,6-tetramethylpiperidide) or LDA (lithium diisopropylamide), being followed by a substitution of the metal atom with an $R_{1a}$ group, then by a Dieckmann condensation or by any other equivalent reaction for obtaining compounds 4 and 5, then by a condensation of the compounds of general formulae 4 and 5, preferably by means of a metallation reaction, to obtain a lactone 3 which is then subjected to an asymmetric reduction to give an enantiomer of compound 1 in which $R_{1b}$ is $R_{1a}$, and said enantiomer can optionally be metallated to obtain an enantiomer in which $R_{1b}$ is different from $R_{1a}$.

Preferably, the method of complete asymmetric synthesis according to the invention comprises 2, 3, 4 or more steps of metallation.

Asymmetric Synthesis from Compounds 4 and/or 5

The invention also relates to a method of asymmetric synthesis of the compounds of formula 1 from compounds 4 and 5, regardless of how they are prepared, in which a condensation of the compounds of general formulae 4 and 5 is carried out, preferably by means of a metallation reaction, to obtain a lactone 3, which is then subjected to an asymmetric reduction to give an enantiomer of compound 1 in which $R_{1b}$ is $R_{1a}$, and said enantiomer can optionally be metallated to obtain an enantiomer 1 in which $R_{1b}$ is different from $R_{1a}$.

Complete Racemic Synthesis

The invention also relates to a method of complete racemic synthesis of the compounds of formula 1 in which $R_{1b}$ is identical to $R'_{1b}$, $R_2$ is identical to $R'_2$ and $R_3$ is identical to $R'_3$, which are also preferred compounds of the invention, in which, starting from compound 8, compound 4 is synthesized as described above, then compound 4 is reduced to obtain compound 9 or compound 10, and a self-condensation is carried out by a reaction known by a person skilled in the art, for example reference 26, and optionally one or more metallation reactions are carried out on $R_{1a}$ to transform it into $R_{1b}$ or on the $CH_3$ group to transform it into $R_{2b}$ or $R'_{2b}$. A metallation reaction on $CH_3$ can be carried out before or after self-condensation.

The invention also relates to a method of racemic synthesis of the compounds of formula 1 in which $R_{1b}$ is identical to $R'_{1b}$, $R_2$ is identical to $R'_2$ and $R_3$ is identical to $R'_3$, which are also preferred compounds of the invention, from compound 4 in which compound 4 is reduced to obtain compound 9 or compound 10, and a self-condensation is carried out by a metallation reaction between $OR_4$ and the reduced $CH_2OH$ or $CH_3$ group and optionally one or more metallation reactions are performed on $R_{1a}$ into transform it to $R_{1b}$ or on the $CH_3$ group to transform it into $R_{2b}$ or $R'_{2b}$.

Synthesis of Compound 7

The invention also relates to a method for the preparation of compound 7, by metallation of compound 8, which is preferably veratric acid, wherein the carboxylic acid function is not protected beforehand; these compounds are useful as synthesis intermediates for preparing pharmaceutical active ingredients in particular of the compounds of general formula 1 according to the invention or of derivatives of quercetin; for example 3,4-dimethoxy-2-methylbenzoic acid is a key synthesis intermediate for inhibitors of HIV proteases; or for preparing phytopharmaceutical active ingredients.

According to a particular embodiment of the invention, veratric acid or preferably a salt thereof is reacted with a lithium derivative, preferably lithium 2,2,6,6-tetramethylpiperidide (LTMP) or lithium diisopropylamide (LDA), without having to protect the carboxylic acid group beforehand (metallation reaction). After adding iodomethane, the compound of general formula 7, in which $R_{1a}$ is a methyl, is obtained. In the present work, the applicant shows that compound 8, which is preferably veratric acid, can be functionalized in position 2 of the ring, even though the acid function is not protected, under certain conditions. Optimization of the conditions shows that the best yield is obtained when metallation is performed with LTMP.

Synthesis of Compound 7b

Next, $R_{1a}$, which is a methyl, can be metallated again, for example with LTMP or LDA, to obtain the compound of general formula 7b, in which $R_{1b}$ is different from $R_{1a}$. The functionalization of the radical $R_{1a}$ can therefore be modulated at this step in the complete synthesis of compounds 1 of the invention. Compound 7b corresponds to the general formula:

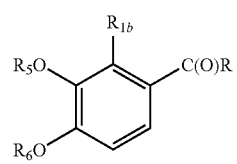

7b in which $R_{1b}$ is a linear or branched alkyl with 1 to 6 carbon atoms, optionally substituted, a linear or branched alkoxy with 1 to 6 carbon atoms, optionally substituted, or an ester, preferably $R_{1b}$ is methyl, ethyl, n-propyl, isopropyl, n-butyl, t-butyl, s-butyl, isobutyl, $R_5$ and $R_6$ are each independently a hydrogen, a linear or branched alkyl with 1 to 6 carbon atoms, optionally substituted, or a protective group of the hydroxy function and $R_7$ is OH, or O (linear or branched alkyl with 1 to 6 carbon atoms optionally substituted).

Example 2 gives details, non-limitatively, of the operating conditions for the metallation of veratric acid into compound 7.

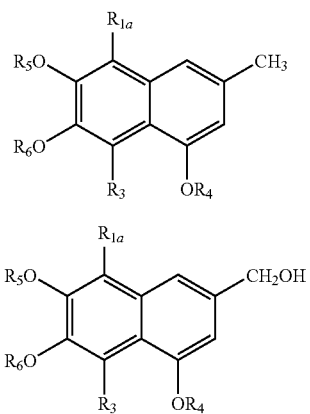

The method according to the invention makes it possible to prepare the compounds of general formula 7 substituted in position 2, in particular with the following atoms or groups: D, Me, Et, Cl, Br, I, MeS, $CO_2H$, CHO, Ph(CHOH), PhNHCO, OH, namely in particular
3,4-dimethoxy-2-methylbenzoic acid,
3,4-dimethoxy-2-ethylbenzoic acid,
2-deuterio-3,4-dimethoxybenzoic acid,
2-chloro-3,4-dimethoxybenzoic acid,
2-bromo-3,4-dimethoxybenzoic acid,
2-iodo-3,4-dimethoxybenzoic acid,
3,4-dimethoxy-2-thiomethylbenzoic acid,
3,4-dimethoxybenzene-1,2-dioic acid,
3-hydroxy-4,5-dimethoxyisobenzofuran-1(3H)-one,
4,5-dimethoxy-3-phenylisobenzofuran-1(3H)-one,
4,5-dimethoxy-2-phenylisoindoline-1,3-dione and
2-hydroxy-3,4-dimethoxybenzoic acid.

Example 5 gives a non-limitative example of operating conditions.

Synthesis of compound 4: the invention also relates to a method for preparing compound 4 starting from the compound of general formula 8 in which $R_5$ and $R_6$ are each independently a protective group of the hydroxy function; and preferably veratric acid or a salt thereof; said method of complete synthesis comprising at least one step of metallation of compound 8 in position 2 of the ring, said step of metallation in position 2 of the aromatic ring of 8 preferably involving the reagent LTMP or LDA, being followed by a substitution of the metal atom with an $R_{1a}$ group, then by a Dieckmann condensation or by any other equivalent reaction for obtaining compound 4.

Synthesis of compound 6: the invention also relates to a method of functionalization by metallation of radical $R_{1a}$ of compound 4, followed by a substitution. According to a particular embodiment, the invention relates to a method of metallation of 8-methyl-4,6,7-trimethoxy-2-naphthoic acid, which is the compound 4 in which $R_{1a}$, $R_4$, $R_5$ and $R_6$ are each independently a methyl and $R_3$ is a hydrogen atom.

Investigations by the applicant show that compound 4 in which $R_{1a}$ is a methyl, can only be metallated on the methyl in position 8 to obtain compounds 4 in which $R_{1a}$ is metallated to a substituent $R_{1b}$ (compound 6).

Metallation in position 3 of compound 6: the invention also relates to a method of metallation in position 3 of a compound of general formula 6 having a substituent that cannot be metallated in position 8 of the ring. Different positions are indicated by atoms H1, H3 and H5 in general formula 6 shown below. According to a particular embodiment of the invention, the invention relates to the preparation of 8-isopropyl-4,6,7-trimethoxy-2-naphthoic acid, which is the compound of general formula 6 in which $R_{1b}$ is an isopropyl group, $R_4$, $R_5$ and $R_6$ are each independently a methyl.

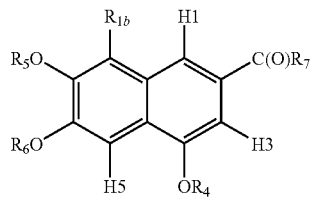

6

The applicant's investigations show that the compound of general formula 6 bearing a substituent that cannot be metallated in position 8 can be metallated in position 3.

The following examples are given purely as a guide and are not to be regarded as limiting in any way.

BRIEF DESCRIPTION OF THE EXAMPLES

Example 1 is an example of complete asymmetric synthesis.

Example 2 gives a racemic synthesis from compound 4.

Example 3 shows a modification of the substituents $R_{2b}$ and $R'_{2b}$ and shows that various substituents can be inserted in this position.

Example 4 describes a method of obtaining compound 6 by metallation of compound 4: Metallation of 8-methyl-4,6,7-trimethoxy-2-naphthoic acid in position 8.

Example 5 describes a method of functionalization in position 3 of compound 6 in which $R_{1b}$ is an isopropyl.

Example 1

Complete Asymmetric Synthesis

Example 1.1

General Procedure for Preparing
3,4-dimethoxybenzoic Acids Substituted in Position
2 and Obtaining Compound 7 by Metallation of a
Particular Compound 8, Veratric Acid LTMP (12 mmol) in THF (20 mL) is added dropwise to a stirred solution of lithium 3,4-dimethoxybenzoate (0.564 g, 3 mmol) (prepared by adding one equivalent of n-BuLi at −78° C. to veratric acid (0.552 g, 3 mmol)) in anhydrous THF (15 mL) at 0° C. After stirring at this temperature for 2 h, the solution is trapped with the electrophile, for example MeI (5 equiv). Stirring is maintained for 1 h, then the solution is left at ambient temperature for 1 h and then heated at 40-66° C. (1 h). After hydrolysis with water (30 mL), the aqueous phase is washed with ether (2×20 mL), acidified with 2M HCl solution (pH=1-2), then extracted with ether (3×30 mL). The organic phase is dried over $MgSO_4$, filtered and concentrated under reduced pressure to give the raw benzoic acids, which are chromatographed on silica gel or recrystallized.

Example 1.2

Preparation of
4,6,7-trimethoxy-8-methyl-2-naphthoic Acid
(Compound 4)

4,6,7-Trimethoxy-8-methyl-2-naphthoic acid (7) is prepared in six steps according to the following reaction diagram. Reduction of 3,4-dimethoxy-2-methylbenzoic acid (1) to aldehyde (2) can be carried out by the Rosenmund reaction ($SOCl_2$ then $H_2$, Pd/$BaSO_4$) (see reference 27). The aldehyde (2) is then reacted with dimethyl succinate (Stobbe reaction) (see reference 28). The coupling product (3) is not isolated but is treated directly with sodium acetate in the presence of acetic anhydride and acetic acid (AcOH/$Ac_2O$ 1:1) to give 4. After saponification, 4-hydroxy-6,7-dimethoxy-8-methyl-2-naphthoic acid (5) is obtained with a yield of 70% (3 steps). After esterification under the conditions described above (90%), compound 6 is hydrolysed to give 4,6,7-trimethoxy-8-methyl-2-naphthoic acid (7) (92%).

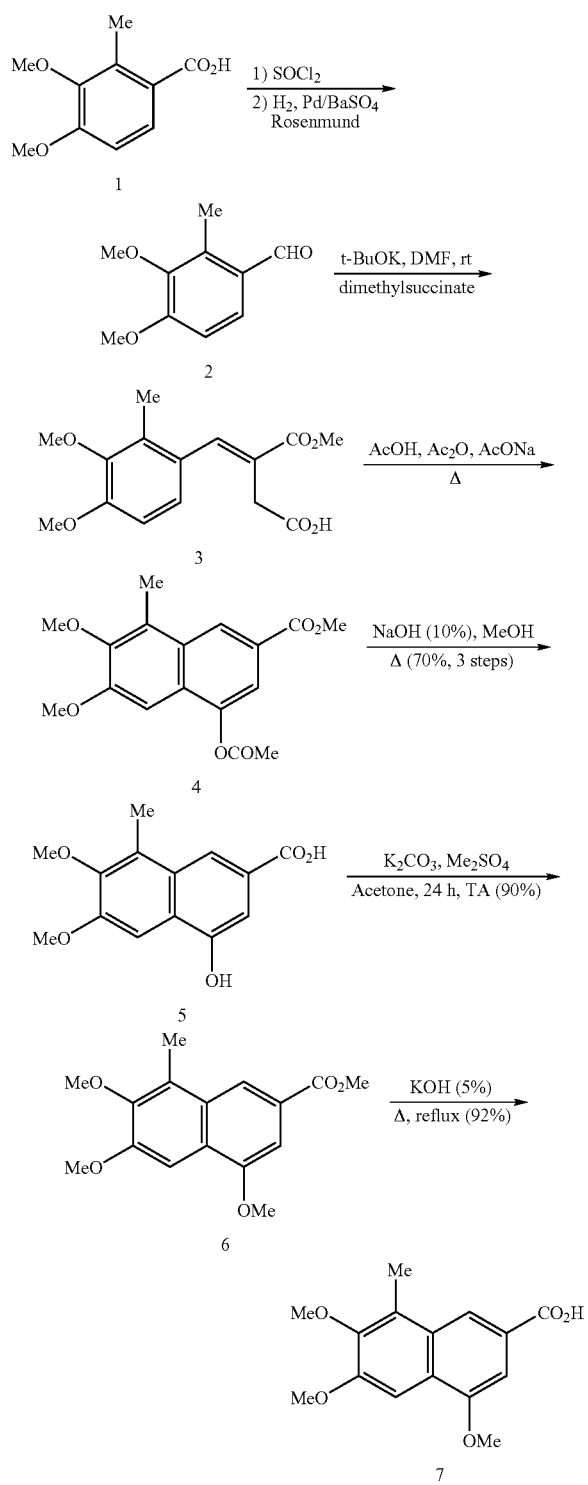

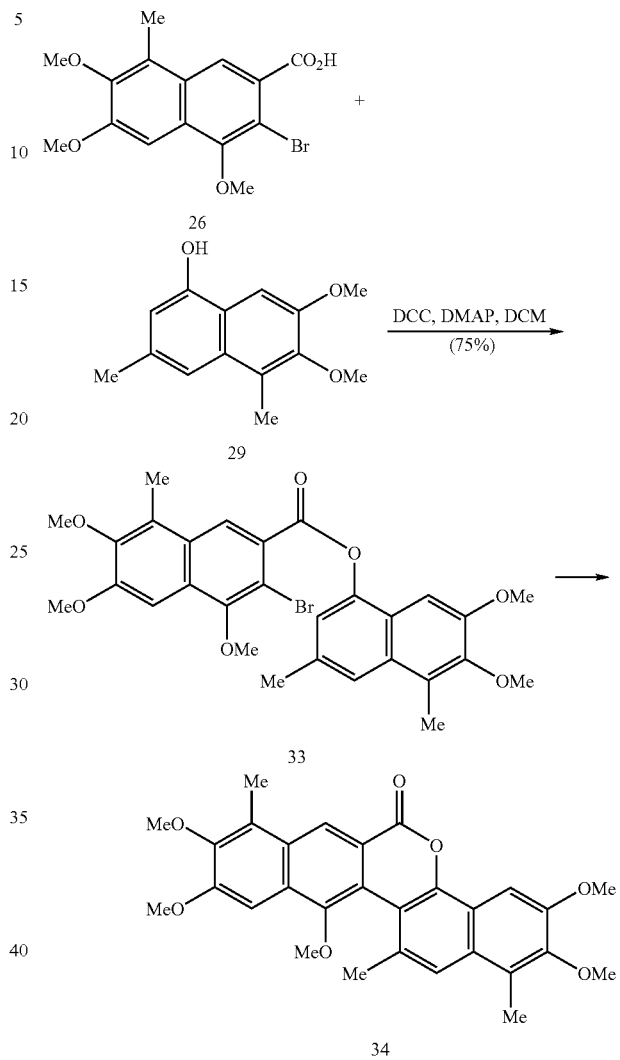

(DMAP) in DCM (see reference 23), lead to the required ester 33 with a yield of 75% after chromatography.

1.4 Asymmetric reduction and metallation in position 8 of $R_{1a}$ and $R_{1b}$.

The asymmetric reduction of the lactone is carried out by methods known by a person skilled in the art, for example employing an asymmetric catalyst, in particular compound 11 described in the present invention, or by using chiral oxazaborolidines.

Example 2

Racemic Synthesis

Example 2.1

4—Synthesis of 3-(hydroxymethyl)-6,7-dimethoxy-5-methylnaphthalen-1-ol (28) and of 6,7-dimethoxy-3,5-dimethylnaphthalen-1-ol (29)

The reduction of 4-hydroxy-6,7-dimethoxy-8-methyl-2-naphthoic acid 4 to alcohol 28 can be carried out either in the presence of $LiAlH_4$ (reference 1) with reflux of THF (90%), 1.3 Preparation of the Lactone (3): Synthesis of 6,7-dimethoxy-3,5-dimethylnaphthalen-1-yl 3-bromo-4,6,7-trimethoxy-8-methyl-2-naphthoate (33) and Cyclization into Lactone The acid 26 and the alcohol 29, in the presence of dicyclohexylcarbodiimide (DCC) and 4-(dimethylamino) pyridine or with the BH$_3$-THF complex at 0° C. in THF (reference 2) (98% raw). The transformation of the alcohol 28 into methylated derivative 29 was investigated by three methods. The reduction can be carried out by catalytic hydrogenation (reference 3) via the bromine derivative or via the tosylated or mesylated derivatives (reference 4). The catalytic reduction by H$_2$, Pd/C (10%) of 28 at 2 bar in EtOH (70° C.) leads to the expected product (35%) (reference 5). In an acid medium (H$_2$, Pd/C 10%, HCl 10%) (reference 1) there is degradation. Moreover, we also tested the reduction of the benzyl group according to McMurray's conditions (reference 7). The starting product is in this case recovered unchanged.

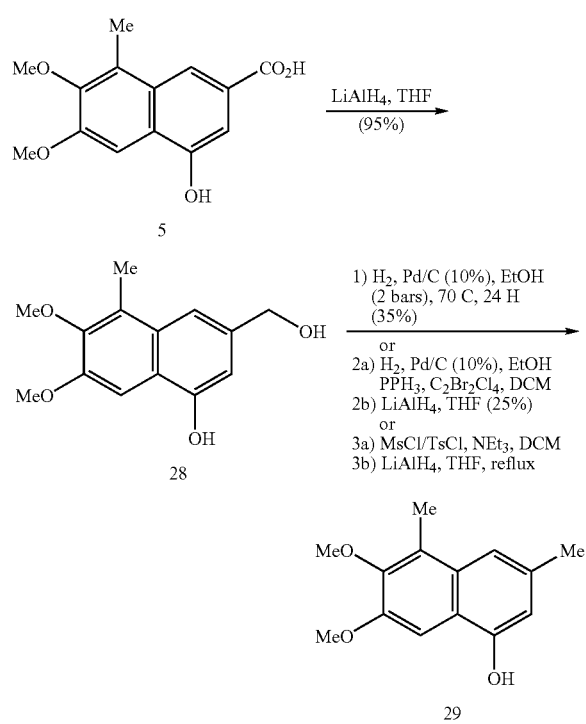

The transformation of the hydroxymethyl function of 28 to halomethyl function was investigated with C$_2$Br$_2$Cl$_4$ (reference 8) or CBr$_4$ (reference 9) as electrophiles in the presence of PPh$_3$ (reference 10). The intermediate obtained is then reduced without purification by LiAlH$_4$ in THF (reference 11). The 6,7-dimethoxy-3,5-dimethylnaphthalen-1-ol (29) is purified by silica chromatography (cyclohexane/ethyl acetate 9:1) with a yield of 25% for the two steps when the electrophile used is C$_2$Br$_2$Cl$_4$ and with a yield of 14% with CBr$_4$. In these reactions, there is also competitive bromination of the phenolic OH function, which explains the poor yields obtained for these transformations (reference 12). Attempts to purify the bromomethylated intermediate failed.

The sulphonates of 28 were prepared under conditions (NEt$_3$, MsCl or TsCl) (reference 13). The unstable tosylates and mesylates are immediately treated with LiAlH$_4$ under THF reflux (reference 14) for the mesylated derivatives or with NaBH$_3$CN in HMPA at 80° C. (reference 15,16) for the tosylated derivatives. In the case of the mesylates, $^1$H NMR analysis of the raw mixture from reduction shows that 29 has indeed been formed, mixed with by-products. 29 is purified by silica gel chromatography.

With TsCl after reduction, $^1$H NMR shows (reference 17) that 2,3-dimethoxy-1,7-dimethylnaphthalen-5-yl-4-methylbenzenesulphonate (30) is formed. Purification by silica gel chromatography (cyclohexane/ethyl acetate 8:2) allows this intermediate to be isolated (22%), which is then deprotected (1M KOH, 90° C.) (reference 17) to give the expected compound 29 quantitatively.

(a) The ditosylated product is also isolated by chromatography (cyclohexane/ethyl acetate 8:2) with a yield of 10%. This product was reduced with NaBH3CN (8 equiv)/HMPA.

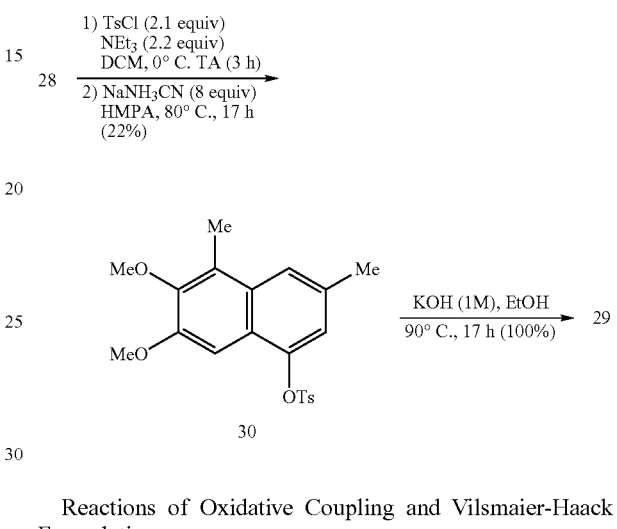

Reactions of Oxidative Coupling and Vilsmaier-Haack Formylation 3-(Hydroxymethyl)-6,7-dimethoxy-5-methylnaphthalen-1-ol (28) treated with di-t-butylperoxide (reference 18) in chlorobenzene leads to 3,6'-bis(hydroxymethyl)-2',3',6,7-tetramethoxy-4',5-dimethyl-2,7'-binaphthyl-1,8'-diol (31) with a yield of 90%. The best results are obtained with mixing at 105° C. for 50 h. At a higher temperature (reflux of the chlorobenzene), there is degradation (reference 19).

6,7-Dimethoxy-3,5-dimethylnaphthalen-1-ol (29) is converted into 2',3',6,7-tetramethoxy-1',3,5'-tetramethyl-2,6'-binaphthyl-1,5'-diol (32) by heating at 200° C. for 30 min without solvent (30%) (Reference 20). Conversion is satisfactory when the reaction time is 4 h (90%). Compounds 31 and 32 are structural analogues of apogossypol (which corresponds to deformylated gossypol). 32 is a particularly preferred compound of the invention.

It has been shown that apogossypol fully retains its activity on proteins of the Bcl-2 family and on various types of cancers.

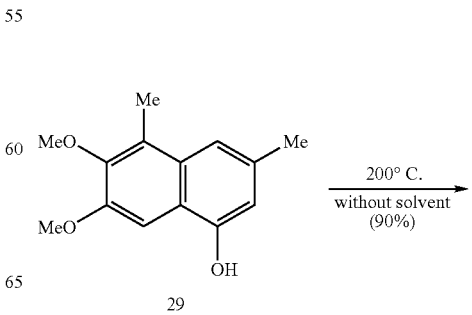

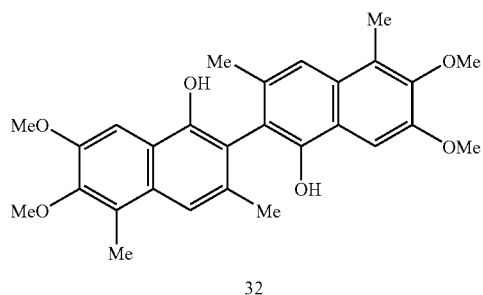

32

Example 3

3,6'-Bis(hydroxymethyl)-2',3',6,7-tetramethoxy-4',5-dimethyl-2,7'-binaphthyl-1,8'-diol (31)

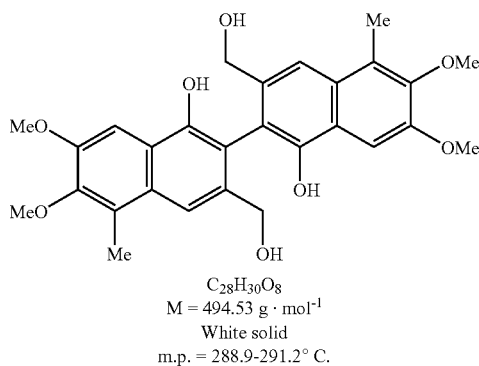 [SMILES: COc1cc2c(O)c(-c3c(CO)cc4c(C)c(OC)c(OC)cc4c3O)c(CO)cc2c(C)c1OC]

C$_{28}$H$_{30}$O$_8$
M = 494.53 g · mol$^{-1}$
White solid
m.p. = 288.9-291.2° C.

Di-t-butyl peroxide (0.07 mL, 0.36 mmol) is added to a solution of 3-(hydroxymethyl)-6,7-dimethoxy-5-methyl-naphthalen-1-ol (90 mg, 0.36 mmol) in chlorobenzene (5 mL) (see reference 24).

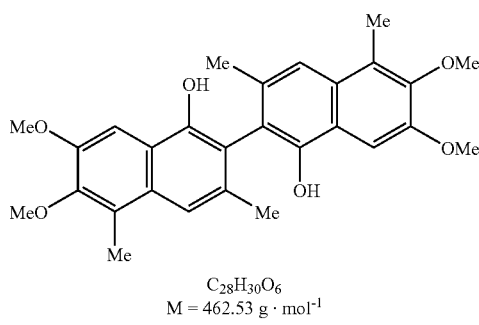

C$_{28}$H$_{30}$O$_6$
M = 462.53 g · mol$^{-1}$
White solid 6,7-Dimethoxy-3,5-dimethylnaphthalen-1-ol (0.232 g, 1 mmol) is heated without solvent at 200° C. for 4 h (reference 20). 2',3',6,7-Tetramethoxy-1'3,5,7'-tetramethyl-2,6'-binaphthyl-1,5'-diol (32) is formed with a yield of 90% (0.209 g, 0.9 mmol). $^1$H NMR (DMSO-d$_6$, 200 MHz) δ 7.48 (s, 2H), 7.45 (s, 2H), 5.22 (s, OH exchangeable with D$_2$O), 4.00 (s, 6H), 3.90 (s, 6H), 2.62 (s, 6H, CH$_3$), 2.14 (s, 6H, CH$_2$). SMHR, [M+H]$^+$ calculated for C$_{28}$H$_{31}$O$_6$: 463.2121. Found: 463.2138.

Example 4

Preparation of Compound 6 by Metallation of Compound 4

Metallation of 8-methyl-4,6,7-trimethoxy-2-naphthoic Acid in Position 8

4.1 Preparation of 8-ethyl-4,6,7-trimethoxy-2-naphthoic Acid External Trapping Technique

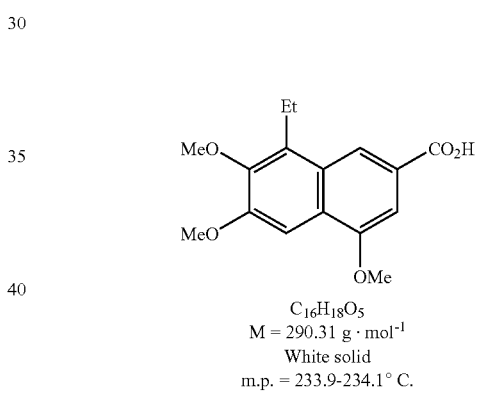

C$_{16}$H$_{18}$O$_5$
M = 290.31 g · mol$^{-1}$
White solid
m.p. = 233.9-234.1° C.

LTMP (7.5 mmol) is added at 0° C. to a solution of 4,6,7-trimethoxy-8-methyl-2-naphthoic acid (0.414 g, 1.5 mmol) in anhydrous THF (30 mL). The mixture is stirred for 2 h at 0° C. then trapped with MeI (0.943 mL, 15 mmol). After 2 h at 0° C., the reaction mixture is heated to ambient temperature and then hydrolysed with 30 mL of water. The aqueous phase is washed with ethyl ether (2×20 mL), acidified with 2M HCl (pH 1-2), then extracted with ethyl ether (3×30 mL). The combined organic phases are dried over MgSO$_4$, filtered, then concentrated under reduced pressure. The residue is recrystallized (cyclohexane/ethyl acetate) to give 8-ethyl-4,6,7-trimethoxy-2-naphthoic acid (3) (0.392 g, 90%). $^1$H NMR (200 MHz, acetone-d$_6$): 8.22 (s, 1H), 7.44 (s, 1H), 7.29 (s, 1H), 3.96 (s, 3H, OCH$_3$), 3.89 (s, 3H, OCH$_3$), 3.78 (s, 3H, OCH$_3$), 3.02 (q, 2H, CH$_2$), 1.16 (t, 3H, CH$_3$). $^{13}$C NMR (100 MHz, DMSO-d$_6$): 167.8, 154.2, 153.2, 146.9, 132.9, 127.0, 126.5, 125.0, 118.5, 102.6, 99.6, 60.6, 55.6, 55.4, 18.6, 15.4. IR (cm$^{-1}$): 2940, 2826, 2637, 1682, 1464. SMHR, [M+H]$^+$ calculated for C$_{16}$H$_{19}$O$_5$: 291.1232. Found: 291.1230.

4.2—Preparation of 4,6,7-trimethoxy-8-((trimethylsilyl)methyl)-2-naphthoic Acid In-Situ Trapping Technique.

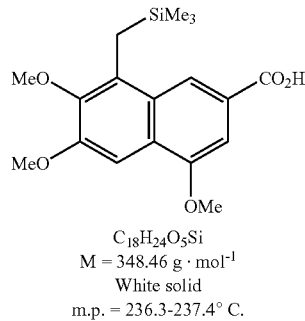 [SMILES: COc1cc2c(OC)cc(C(=O)O)cc2c(C[Si](C)(C)C)c1OC]

$C_{18}H_{24}O_5Si$
M = 348.46 g·mol$^{-1}$
White solid
m.p. = 236.3-237.4° C.

4,6,7-Trimethoxy-8-methyl-2-naphthoic acid (1) (0.276 g, 1 mmol) is added at −78° C. to a mixture containing the base LTMP (4.2 mmol) and TMSCl (0.998 mL, 5.7 mmol) in anhydrous THF (10 mL). The reaction mixture is stirred at −78° C. for 1 h then gradually heated to ambient temperature over 3 h. After hydrolysis, the reaction mixture is treated with a solution of 2M NaOH (pH 10). The aqueous phase is washed with ethyl ether (2×15 mL), acidified with 2M HCl (pH 1-2) then extracted with dichloromethane (3×20 mL). The combined organic phases are dried over MgSO$_4$, filtered, then concentrated under reduced pressure. The residue is purified by recrystallization (cyclohexane/ethyl acetate) to give 4,6,7-trimethoxy-8-((trimethylsilyl)methyl)-2-naphthoic acid (2) (0.307 g, 88%). $^1$H NMR (200 MHz, CDCl$_3$): 8.37 (s, 1H), 7.44 (s, 1H), 7.40 (s, 1H), 4.07 (s, 3H, OCH$_3$), 4.03 (s, 3H, OCH$_3$), 3.88 (s, 3H, OCH$_3$), 2.63 (s, 2H, CH$_2$), 0.02 (s, 9H, Si(CH$_3$)$_3$). SMHR, [M+H]$^+$ calculated for C$_{18}$H$_{25}$O$_5$Si: 349.1471. Found: 349.1468.

Example 5

Method of Functionalization in Position 3 of Compound 6 in which $R_{1b}$ is an Isopropyl 3-Deuterio-8-isopropyl-4,6,7-trimethoxy-2-naphthoic Acid. Metallation of 8-isopropyl-4,6,7-trimethoxy-2-naphthoic Acid

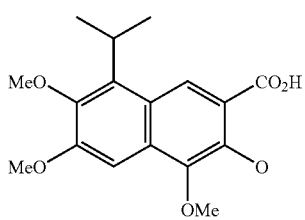

n-BuLi (3.2 mL, 5 mmol of a 1.6 M solution in hexane) is added dropwise at 0° C. to tetramethylpiperidine (5 mmol, 0.850 mL) in solution in anhydrous THF (10 mL). After stirring for 30 minutes at 0° C., 8-isopropyl-4,6,7-trimethoxy-2-naphthoic acid (0.304 g, 1 mmol) in THF (5 mL) is added slowly and the reaction mixture is stirred for 2 h. After adding D$_2$O (0.1 mL, 5 mmol) dissolved in THF (1.5 mL) and stirring for 1 h at 0° C., the reaction mixture is heated to ambient temperature and then hydrolysed (20 mL of water). The phases are separated, the aqueous phase is washed with diethyl ether (20 mL), acidified with 2M HCl (pH 1) and extracted with diethyl ether (3×20 mL). The combined organic phases are dried over magnesium sulphate, filtered and concentrated under reduced pressure to give 24% conversion to deuterated product in position 3 of the ring.

REFERENCES

[1] (a) Edward, J. D. Jr; Cashaw, J. L. *J. Am. Chem. Soc.* 1957, 79, 2283. (b) Motomura, T.; Nakamura, H.; Suginome, M.; Murakami, M.; Ito, Y. *Bull. Chem. Soc. Jpn.* 2005, 78, 142.

[2] Ashkenazi, N.; Milstein, D. *J. Am. Chem. Soc.* 2000, 126, 8797.

[3] (a) Rylander, P. N. *Hydrogenation Methods* New Jersey, 1988, p. 126. (b) Hudlický, M. *Reductions in Organic Chemistry* 1996, p. 1. (c) Larock, R. C. *Comprehensive Organic Transformations: A Guide to Functional Group Preparations* 1999.

[4] (a) Sawada, Y.; Kayakiri, H.; Abe, Y.; Imai, K.; Mizutani, T.; Inamura, N.; Asano, M.; Aramori, I.; Hatori, C; Katayama, A.; Oku, T.; Tanaka, H. *J. Med. Chem.* 2004, 47, 1617. (b) Hansen, A. L.; Skrydstrup, T. *Org. Lett.* 2005, 7, 5585.

[5] (a) Conversion is total. The reaction also leads to by-products. (b) In ethyl acetate, the starting product is recovered unchanged.

[6] (a) Meyers, A. I.; Willemsen, J. J. *Tetrahedron* 1998, 54, 10493. (b) Moorlag, H.; Meyers, A. I. *Tetrahedron Lett.* 1993, 34, 6993.

[7] Generation in situ of H$_2$ by addition of Et$_3$SiH to Pd/C catalyst: Mandal, P. K.; McMurray, J. S. *J. Org. Chem.* 2007, 72, 6599.

[8] (a) Bringmann, G.; Ochse, M.; Gotz, R. *J. Org. Chem.* 2000, 65, 2069. (b) Bringmann, G.; Hamm, A.; Schraut, M. *Org. Lett.* 2003, 5 (6), 2805.

[9] (a) Baughman, T. W.; Sworen, J. C; Wagener, K. B. *Tetrahedron* 2004, 60, 10943. (b) Lan, A. J. Y.; Heuckeroth, R. O.; Mariano, P. S. *J. Am. Chem. Soc.* 1987, 109, 2738.

[10] (a) Trost, B. M.; Yeh, V. S. C; Ito, H.; Bremeyer, N. *Org. Lett.* 2002, 4, 2621. (b) Owada, J.; Murasaki, C; Yamazaki, T.; Ichihara, S.; Umeda, I.; Shimma, N. *Bioorg. Med. Chem. Lett.* 2002, 12, 2775. (c) Vögtle, F.; Eisen, N.; Franken, S.; Bullesbach, P.; Puff, H. *J. Org. Chem.* 1987, 52, 5560. (d) Doxsee, K. M.; Feigel, M.; Stewart, K. D.; Canary, J. W.; Knobler, C. B.; Cram, D. J. *J. Am. Chem. Soc.* 1987, 109, 3098. (e) Cram, D. J.; Helgeson, R. C; Peacock, S. C; Kaplan, L. J.; Domeier, L. A.; Moreau, P.; Koga, K.; Mayer, J. M.; Chao, Y.; Siegel, M. G.; Hoffman, D. H.; Sogah, G. D. Y. *J. Org. Chem.* 1978, 43, 1930.

[11] (a) Cram, D. J.; Helgeson, R. C; Peacock, S. C; Kaplan, L. J.; Domeier, L. A.; Moreau, P.; Koga, K.; Mayer, J. M.; Chao, Y.; Siegel, M. G.; Hoffman, D. H.; Sogah, G. D. Y. *J. Org. Chem.* 1978, 43, 1930. (b) Bringmann, G.; Ochse, M.; Götz, R. *J. Org. Chem.* 2000, 65, 2069. (c) Bringmann, G.; Hamm, A.; Schraut, M. *Org. Lett.* 2003, 5 (6), 2805.

[12] (a) Wiley, G. A.; Hershkowitz, R. L.; Rein, B. M.; Chung, B. C. *J. Am. Chem. Soc.* 1964, 86, 964. (b) Takaya, H.; Akutagawa, S.; Noyori, R. *Org. Syn. Coll. Vol.* 8 1993, 57.

[13] (a) Sawada, Y.; Kayakiri, H.; Abe, Y.; Imai, K.; Mizutani, T.; Inamura, N.; Asano, M.; Aramori, I.; Hatori, C; Katayama, A.; Oku, T.; Tanaka, H. *J. Med. Chem.* 2004, 47, 1617. (b) Hansen, A. L.; Skrydstrup, T. *Org. Lett.* 2005, 7, 5585.

[14] Rizzacasa, M. A.; Sargent, M. V. *J. Chem. Soc. Perkin Trans.* 1 1991, 845.

[15] (a) Hutchins, R. O.; Milewski, C. A.; Maryanoff, B. E. *Org. Syn. Coll. Vol.* 6 1988, p. 376. (b) Hutchins, R. O.; Kandasamy, D.; Maryanoff, C. A.; Masilamani, D.; Maryanoff, B. E. *J. Org. Chem.* 1977, 42, 82.

[16] The function CH$_2$OTs can be reduced by LAH under THF reflux: Fisnerova, L.; Kakac, B.; Nemecek, O.; Simek, A.; Vejdelek, Z. J. *Coll. Czech. Chem. Commun.* 1967, 32, 4082.

[17] Mewshaw, R. E.; Edsall, R. J., Jr.; Yang, C.; Manas, E. S.; Xu, Z. B.; Henderson, R. A.; Keith, J. C., Jr.; Harris, H. A. *J. Med. Chem.* 2005, 48, 3953.

[18] (a) Ognyanov, V. I.; Petrov, O. S.; Tiholov, E. P.; Molloy, N. M. *Helv. Chim. Acta* 1989, 72, 353. (b) Armstrong, D. R.; Cameron, C; Nonhebel, D. C; Perkins, P. G. *J. Chem. Soc, Perkin Trans.* 2 1983, 563. (c) Armstrong, D. R.; Breckenbridge, R. J.; Cameron, C.; Nonhebel, D. C.; Pauson, P. L.; Perkins, P. G. *Tetrahedron Lett.* 1983, 24, 1071.

[19] (a) Armstrong, D. R.; Cameron, C; Nonhebel, D. C.; Perkins, P. G. *J. Chem. Soc., Perkin Trans.* 2 1983, 563. (b) Armstrong, D. R.; Breckenbridge, R. J.; Cameron, C.; Nonhebel, D. C.; Pauson, P. L.; Perkins, P. G. *Tetrahedron Lett.* 1983, 24, 1071.

[20] Edwards Jr., J. D.; Cashaw, J. L. *J. Am. Chem. Soc.* 1957, 79, 2283.

[21] (cf. Edwards, J. D. *J. Am. Chem. Soc.* 1958, 80, 3798-3799).

[22] (a) Meyers, A. I.; Willemsen, J. J. *Tetrahedron Lett.* 1996, 37, 791. (b) Meyers, A. I.; Willemsen, J. *J. Chem. Commun.* 1573. (c) Meyers, A. I.; Willemsen, J. *J. Tetrahedron* 1998, 54, 10493.

[23] Bringmann, G.; Menche, D.; Muhlbacher, J.; Reichert, M.; Saito, N.; Pfeiffer, S. S.; Lipshutz, B. H. *Org. Lett.* 2002, 4, 2833

[24] (a) Ognyanov, V. I.; Petrov, O. S.; Tiholov, E. P.; Molloy, N. M. *Helv. Chim. Acta* 1989, 72, 353. (b) Armstrong, D. R.; Cameron, C.; Nonhebel, D. C.; Perkins, P. G. *J. Chem. Soc., Perkin Trans.* 2 1983, 563. (c) Armstrong, D. R.;

[25] Parham, W. E.; Bradcher, C. K. *Acc. Chem. Res.* 1982, 15, 300;

[26] Ognyanov, V. I.; Petrov, O. S.; Tiholov, E. P.; Mollov, N. M. *Helv. Chim. Acta* 1989, 72, 353 Edwards Jr., J. D.; Cashaw, J. L. *J. Am. Chem. Soc.* 1957, 79, 2283;

[27] Rosenmund, K. W. *Ber. Deutsch. Chem. Gesellsch.* 1918, 51, 1585. Recent references cited in (b) Sakata, Y.; Ponec, V. *Applied Catalysis A: General* 1998, 166, 173-184. or according to Grundmann. Fieser, L. F.; Fieser, M. *Advanced Organic Chemistry*, p 403 (New York, 1961);

[28] Meyers, A. I.; Willemsen, J. J. *Tetrahedron* 1998, 54, 10493. (b) See also: Edward, J. D. Jr.; Cashaw, J. L. *J. Am. Chem. Soc.* 1957, 79, 2283).

Breckenbridge, R. J.; Cameron, C; Nonhebel, D. C.; Pauson, P. L.; Perkins, P. G. *Tetrahedron Lett.* 1983, 24, 1071

The invention claimed is:

1. A compound of general formula (1)

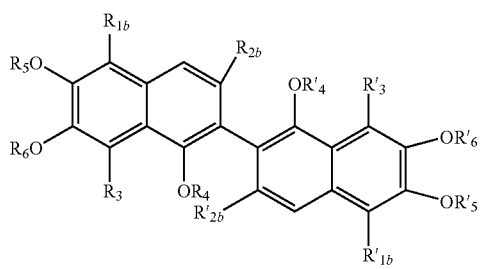

(1)

in which $R_{1b}$ and $R'_{1b}$ are each independently methyl, ethyl, n-propyl, n-butyl, t-butyl, s-butyl, pentyl or hexyl, $R_{2b}$ and $R'_{2b}$ are each independently a linear or branched alkyl with 1 to 6 carbon atoms, optionally substituted, or an ester, $R_3$ and $R'_3$ are each independently a hydrogen, CHO, $CR_8=NR_9$ or $C(O)OR_{10}$ group in which $R_8$, $R_9$ and $R_{10}$ are independently a hydrogen atom or a linear or branched alkyl with 1 to 20 carbon atoms, optionally substituted, or a linear or branched alkenyl with 2 to 20 carbon atoms, optionally substituted; and $R_4$, $R'_4$, $R_5$, $R'_5$, $R_6$ and $R'_6$ are each a hydrogen, or a protective group of the hydroxy function, gossypol, apogossypol and the compounds in which simultaneously $R_{1b}$, $R'_{1b}$ are ethyl and $R_{2b}$, $R'_{2b}$ are methyl being excluded, or one of its enantiomers, or one of its salts, or a salt of one of its enantiomers.

2. The compound according to claim 1, wherein $R_3$ and $R'_3$ are identical.

3. The compound according to claim 1, wherein $R_{2b}$ and $R'_{2b}$ are identical.

4. The compound according to claim 1, wherein $R_{1b}$ and $R'_{1b}$ are identical.

5. The compound according to claim 1, wherein $R_{1b}$ and $R'_{1b}$ are each independently methyl, n-propyl, n-butyl, s-butyl, t-butyl, $R_{2b}$ and $R'_{2b}$ are each methyl, and $R_3$ and $R'_3$ are each independently a hydrogen or CHO.

6. The compound according to claim 1, wherein $R_{1b}$ and $R'_{1b}$ are each methyl, $R_{2b}$ and $R'_{2b}$ are each independently methyl, ethyl, n-propyl, isopropyl, n-butyl, s-butyl, t-butyl, isobutyl, and $R_3$ and $R'_3$ are each independently a hydrogen or CHO.

7. The compound according to claim 1, wherein $R_{1b}$ and $R'_{1b}$ are each ethyl, $R_{2b}$ and $R'_{2b}$ are each independently ethyl, n-propyl, isopropyl, n-butyl, s-butyl, t-butyl, isobutyl, and $R_3$ and $R'_3$ are each independently a hydrogen or CHO.

8. The compound according to claim 1, wherein $R_{1b}$ and $R'_{1b}$ are each n-propyl, $R_{2b}$ and $R'_{2b}$ are each independently methyl, ethyl, n-propyl, isopropyl, n-butyl, s-butyl, t-butyl, isobutyl, $R_3$ and $R'_3$ are each independently a hydrogen or CHO.

9. A method of asymmetric synthesis of the compounds of formula (1):

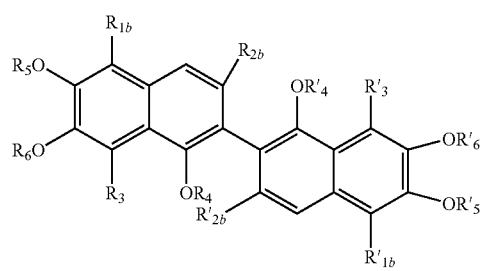

(1)

in which $R_{1b}$ and $R'_{1b}$ are each independently a linear or branched alkyl with 1 to 6 carbon atoms, optionally substituted, a linear or branched alkoxy with 1 to 6 carbon atoms, optionally substituted, or an ester; $R_{2b}$ and $R'_{2b}$ are each independently a linear or branched alkyl with 1 to 6 carbon atoms, optionally substituted, a linear or branched alkoxy with 1 to 6 carbon atoms, optionally substituted, or an ester; $R_3$ and $R'_3$ are each independently a hydrogen, CHO, $CR_8=NR_9$ or $C(O)OR_{10}$ group in which $R_8$, $R_9$ and $R_{10}$ are independently a hydrogen atom or a linear or branched alkyl with 1 to 20 carbon atoms, optionally substituted, or a linear or branched alkenyl with 2 to 20 carbon atoms, optionally substituted; $R_4$, $R'_4$, $R_5$, $R'_5$, $R_6$ and $R'_6$ are each independently a hydrogen, a linear or branched alkyl with 1 to 20 carbon atoms, optionally substituted, or a protective group of the hydroxy function, gossypol and apogossypol being excluded;

by condensation of the compounds of general formulae (4) and (5),

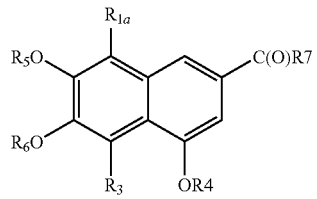
(4)

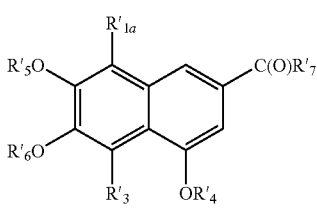
(5)

in which $R_{1a}$ and $R'_{1a}$ are each independently a group that can undergo metallation, $R_3$ and $R'_3$ are each independently a hydrogen or CHO or any group capable of being transformed in vivo to release a hydrogen or a CHO $R_4$, $R'_4$, $R_5$, $R'_5$, $R_6$ and $R'_6$ are each independently a hydrogen, a linear or branched alkyl with 1 to 6 carbon atoms, optionally substituted, or a protective group of the hydroxy function, and $R_7$ is OH, or O (linear or branched alkyl with 1 to 6 carbon atoms), to obtain a lactone (3)

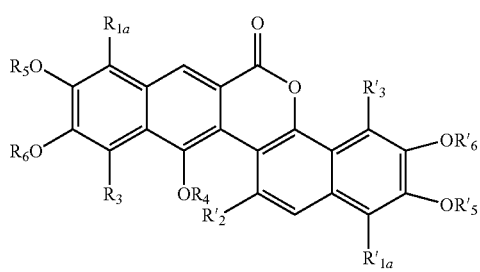
(3)

in which $R_{1a}$ and $R'_{1a}$, $R_3$ and $R'_3$, $R_4$, $R'_4$, $R_5$, $R'_5$, $R_6$ and $R'_6$ are as defined above and $R'_2$ is a linear or branched alkyl with 1 to 6 carbon atoms, optionally substituted, a linear or branched alkoxy with 1 to 6 carbon atoms, optionally substituted, said lactone being subjected to an asymmetric reduction to give an enantiomer of compound (1)

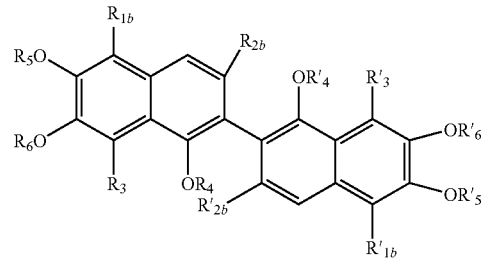

in which $R_3$, $R'_3$, $R_4$, $R'_4$, $R_5$, $R'_5$, $R_6$ and $R'_6$ are as defined above, $R_{1b}$ is $R_{1a}$ or a linear or branched alkyl with 1 to 6 carbon atoms, optionally substituted, a linear or branched alkoxy with 1 to 6 carbon atoms, optionally substituted, or an ester, $R_{2b}$ and $R'_{2b}$ are each independently a linear or branched alkyl with 1 to 6 carbon atoms, optionally substituted, a linear or branched alkoxy with 1 to 6 carbon atoms, optionally substituted, or an ester.

10. A method of racemic synthesis of the compounds of formula (1)

(1)

in which $R_{1b}$ is identical to $R'_{1b}$, $R_2$ is identical to $R'_2$ and $R_3$ is identical to $R'_3$, and compound (4)

(4)

is reduced to obtain the compound of general formula (9) or the compound of general formula (10), (10)

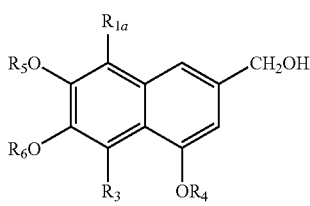

(9)

in which $R_{1a}$ is a group that can undergo metallation, $R_3$ is a hydrogen, CHO, $CR_8$=$NR_9$ or $C(O)OR_{10}$ group in which $R_8$, $R_9$ and $R_{10}$ are independently a hydrogen atom or a linear or branched alkyl with 1 to 20 carbon atoms, optionally substituted, or a linear or branched alkenyl with 2 to 20 carbon atoms, optionally substituted; and $R_4$, $R_5$ and $R_6$ are each independently a hydrogen, a linear or branched alkyl with 1 to 6 carbon atoms, optionally substituted, or a protective group of the hydroxy function and a self-condensation is carried out.

11. The method according to claim 9, wherein compounds (4) and (5) are prepared from the compound of general formula (8)

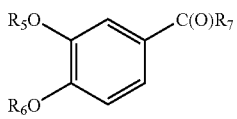

(8)

in which $R_5$ and $R_6$ are each independently a protective group of the hydroxy function; then at least one step of metallation of compound (8) in position 2 of the ring is carried out, said step of metallation in position 2 of the ring (8) being followed by a substitution of the metal atom with an $R_{1a}$ group, then by a Dieckmann condensation or by any other equivalent reaction for obtaining compounds (4) and (5), said method being a method of complete synthesis of the compounds of general formula (1).

12. The method according to claim 9, wherein, synthesis of the compound of general formula (7) is carried out by metallation of compound (8),

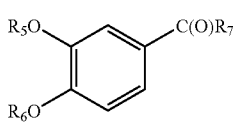

(8)

the carboxylic acid function of which is not protected beforehand, in the presence of a lithium derivative, and addition of iodomethane to obtain the compound of general formula (7)

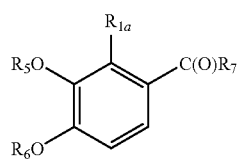

(7)

in which $R_{1a}$ is a methyl and optionally subsequent metallation to obtain compound (7) in which $R_{1a}$ is transformed to $R_{1b}$ other than methyl in particular a linear or branched alkyl with 2 to 6 carbon atoms, optionally substituted, a linear or branched alkoxy with 1 to 6 carbon atoms, optionally substituted, or an ester, and then a condensation is carried out to obtain compound (4).

13. A method comprising at least one compound according to claim 1, or at least one enantiomer thereof, or a salt of such a compound, or a prodrug of such a compound.

14. A pharmaceutical composition comprising at least one compound according to claim 1, or at least one enantiomer thereof, or a salt of such a compound, or a prodrug of such a compound, in combination with any pharmaceutically acceptable excipient.

15. A method for treating cancer selected from colon cancer or colorectal cancer, a melanoma, a lung cancer, a glioblastoma, an adenocarcinoma, a leukaemia, a prostate cancer or a breast cancer, or a viral disease comprising the administration to a subject in need thereof of at least one compound according to claim 1, of an enantiomer of such a compound, of a salt of such a compound or of such an enantiomer, or of a prodrug of such a compound or of such an enantiomer.

16. A contraceptive product or medication comprising at least one compound according to claim 1, of an enantiomer of such a compound, a salt of such a compound or of such an enantiomer, or a prodrug of such a compound or of such an enantiomer.

17. The method according to claim 15, wherein said viral disease is caused by a virus selected from the group consisting of herpes simplex type 2, influenza, parainfluenza, and HIV-1, and said subject may be refractory to other treatments.

18. A phytopharmaceutical composition comprising at least one compound according to claim 1, or at least one enantiomer thereof, or a salt of such a compound, or a prodrug of such a compound, in combination with any phytopharmaceutically acceptable excipient.

19. An antifungal product comprising a compound according to claim 1, or at least one enantiomer thereof, or a salt of such a compound, or a prodrug of such a compound.

20. The compound according to claim 1, wherein $R_{2b}$ and $R'_{2b}$ are each independently methyl, ethyl, n-propyl, isopropyl, n-butyl, s-butyl, t-butyl, isobutyl, pentyl or hexyl.

21. The method according to claim 9, wherein $R_{1b}$ and $R'_{1b}$ are each independently methyl, ethyl, n-propyl, isopropyl, n-butyl, t-butyl, s-butyl, isobutyl, pentyl or hexyl.

22. The method according to claim 9, wherein $R_{2b}$ and $R'_{2b}$ are each independently methyl, ethyl, n-propyl, isopropyl, n-butyl, s-butyl, isobutyl, t-butyl, pentyl or hexyl.

23. The method according to claim 9, wherein $R_{1a}$ and $R'_{1a}$ are methyl.

24. The method according to claim 9, wherein the condensation of the compounds of general formulae (4) and (5) is carried out by means of a metallation reaction.

25. The method according to claim 9, wherein the enantiomer of compound (1) is metallated to obtain an enantiomer in which $R_{1b}$ is different from $R_{1a}$.

26. The method according to claim 10, wherein $R_{1a}$ is methyl.

27. The method according to claim 10, wherein one or more metallation reactions are carried out after the self condensation step is carried out.

28. The method according to claim 9, wherein, synthesis of the compound of general formula (7) is carried out by metallation of compound (8),

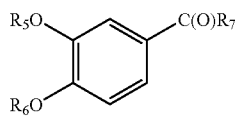
(8)

the carboxylic acid function of which is not protected beforehand, in the presence of lithium 2,6-tetramethylpiperidide (LIMP) or lithium diisopropylamide (LDA), and addition of iodomethane to obtain the compound of general formula (7)

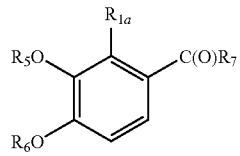
(7)

in which $R_{1a}$ is a methyl and optionally subsequent metallation to obtain compound (7) in which $R_{1a}$ is transformed to $R_{1b}$ other than methyl in particular a linear or branched alkyl with 2 to 6 carbon atoms, optionally substituted, a linear or branched alkoxy with 1 to 6 carbon atoms, optionally substituted, or an ester, and then a condensation is carried out to obtain compound (4).

29. A method for treating or inhibiting the over-expression proteins of the Bcl-2 family in a subject comprising:
administering to said subject at least one compound according to claim 1, of an enantiomer of such a compound, of a salt of such a compound or of such an enantiomer, or of a prodrug of such a compound or of such an enantiomer.

30. The method according to claim 29, wherein the method treats the over-expression proteins of the Bcl-2 family in said subject.

* * * * *

UNITED STATES PATENT AND TRADEMARK OFFICE
CERTIFICATE OF CORRECTION

PATENT NO. : 8,455,540 B2
APPLICATION NO. : 12/746339
DATED : June 4, 2013
INVENTOR(S) : Mortier et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Eighth Day of September, 2015

Michelle K. Lee
*Director of the United States Patent and Trademark Office*